(12) United States Patent
Keeling et al.

(10) Patent No.: US 10,124,022 B2
(45) Date of Patent: Nov. 13, 2018

(54) COMPOSITIONS AND METHODS FOR ENHANCING THE EFFECTIVENESS OF SYSTEMIC, HIPEC, IP, AND RELATED CANCER TREATMENTS

(71) Applicant: ChemoTherapeutics, LLC, Bridgeville, PA (US)

(72) Inventors: Gary Keeling, Bridgeville, PA (US); Keith B. Hoffman, Santa Rosa, CA (US)

(73) Assignee: ChemoTherapeutics, LLC, Bridgeville, PA (US)

(*) Notice: Subject to any disclaimer, the term of this patent is extended or adjusted under 35 U.S.C. 154(b) by 0 days.

(21) Appl. No.: 15/585,053

(22) Filed: May 2, 2017

(65) Prior Publication Data
US 2017/0232037 A1    Aug. 17, 2017

Related U.S. Application Data

(62) Division of application No. 13/812,120, filed as application No. PCT/US2011/045247 on Jul. 25, 2011, now Pat. No. 9,669,053.

(60) Provisional application No. 61/367,820, filed on Jul. 26, 2010.

(51) Int. Cl.
| | | |
|---|---|---|
| A61K 31/35 | (2006.01) | |
| A61K 31/352 | (2006.01) | |
| A61K 31/353 | (2006.01) | |
| A61K 31/375 | (2006.01) | |
| A61K 31/407 | (2006.01) | |
| A61K 33/04 | (2006.01) | |
| A61K 33/24 | (2006.01) | |
| A61K 45/06 | (2006.01) | |
| A61N 5/10 | (2006.01) | |

(52) U.S. Cl.
CPC ............ *A61K 33/04* (2013.01); *A61K 31/352* (2013.01); *A61K 31/353* (2013.01); *A61K 31/375* (2013.01); *A61K 31/407* (2013.01); *A61K 33/24* (2013.01); *A61K 45/06* (2013.01); *A61N 5/10* (2013.01)

(58) Field of Classification Search
CPC .... A61K 33/04; A61K 31/352; A61K 31/375; A61K 31/407; A61K 33/24; A61K 45/06
IPC ................ A61K 33/04,31/352, 31/375, 31/407, 33/24, 45/06
See application file for complete search history.

(56) References Cited

U.S. PATENT DOCUMENTS

| | | | |
|---|---|---|---|
| 5,639,787 A | 6/1997 | Riordan et al. | |
| 5,811,410 A | 9/1998 | Falk et al. | |
| 6,426,076 B1 | 7/2002 | Pascoe | |
| 6,656,509 B1 | 12/2003 | Stiefel et al. | |
| 6,821,536 B2* | 11/2004 | Lines | A23L 33/105 426/541 |
| 7,745,486 B2* | 6/2010 | Lines | A61K 31/352 514/355 |
| 8,440,704 B2* | 5/2013 | Lines | A61K 31/352 514/355 |
| 9,669,053 B2* | 6/2017 | Keeling | A61K 31/352 |
| 2003/0206895 A1* | 11/2003 | Cavazza | A61K 31/35 424/94.1 |
| 2006/0229360 A1 | 10/2006 | Gilloteaux et al. | |
| 2006/0275504 A1 | 12/2006 | Chen | |
| 2007/0043110 A1 | 2/2007 | Gilloteaux et al. | |
| 2008/0015247 A1* | 1/2008 | Lines | A61K 31/352 514/456 |
| 2010/0160245 A1* | 6/2010 | Lines | A61K 31/352 514/27 |

OTHER PUBLICATIONS

Grunicke et al., Advances in Enzyme Regulation vol. 28, pp. 201-216. Published 1989.*
Aalinkeel et al., The dietary bioflavonoid, quercetin, selectively induces apoptosis of prostate cancer cells by down-regulating the expression of heat shock protein 90, Prostate, vol. 68, No. 16, pp. 1773-1789, 2008.
Abdel-Latif et al., Vitamin C Enhances Chemosensitiztion of Esophageal Cancer Cells in Vitro, Journal of Chemotherapy, vol. 17, No. 5, pp. 539-549 (2005).
Asea et al., Effects of the flavonoid drug quercetin on the response of human prostate tumours to hyperthermia in vitro and in vivo, Int J Hyperthermia. Jul.-Aug. 2001;17(4):347-56.
Autunes et al., Protective effects of vitamin c against cisplatin-induced nephrotoxicity and lipid peroxidation in adult rats: a dose-dependent study, Pharmacol Res. Apr. 2000;41(4):405-11.
Behling et al., Comparative study of multiple dosage of quercetin against cisplatin-induced nephrotoxicity and oxidative stress in rat kidneys, Pharmacol Rep. Jul.-Aug. 2006;58(4):526-32.
Berenbaum, Synergy, additivism and antagonism in immunosuppression. A critical review, Clin Exp Immunol. Apr. 1977; 28(1): 1-18.
Bhattacharya et al., Tumor vascular maturation and improved drug delivery induced by methylselenocysteine leads to therapeutic synergy with anticancer drugs, Clinical Cancer Research, vol. 14, No. 12, pp. 3926-3932, 2008.

(Continued)

*Primary Examiner* — Timothy P Thomas
*Assistant Examiner* — George W Kosturko
(74) *Attorney, Agent, or Firm* — Bret E. Field; Bozicevic, Field & Francis LLP

(57) ABSTRACT

Methods for treating cancers, tumors, and neoplasms using a composition comprising one or more generally regarded as safe (GRAS) compounds selected from the group of components consisting of vitamins, selenium, fatty acids, fatty acid salts, and fatty acid esters, and mixtures of two or more said components, either as a stand-alone treatment or in combination with one or more anti-cancer drugs or devices or other anti-neoplastic agents, treatments, or devices are provided. In some instances, concomitant hyperthermia therapy is employed. Also provided are compositions and kits containing the compositions, for implement various aspects of the invention.

13 Claims, 24 Drawing Sheets

(56) References Cited

OTHER PUBLICATIONS

Bhattacharya et al., Selenite treatment inhibits LAPC-4 tumor growth and prostate-specific antigen secretion in a xenograft model of human prostate cancer, Int J Radiat Oncol Biol Phys. Nov. 1, 2008;72(3):935-40.

Borek et al., Selenium and vitamin E inhibit radiogenic and chemically induced transformation in vitro via different mechanisms, Proceedings of the National Academy of Sciences of the United States of America, vol. 83, No. 5, pp. 1490-1494, 1986.

Calviello et al., Docosahexaenoic acid enhances the susceptibility of human colorectal cancer cells to 5-fluorouracil, Cancer Chemotherapy and Pharmacology, vol. 55, No. 1, pp. 12-20, 2005.

Cárcamo et al., Vitamin C is a kinase inhibitor dehydroascorbic acid inhibits IkappaBalpha kinase beta, Mollecular and Cellular Biology, vol. 24, No. 15, pp. 6645-6652, 2004.

Casciari et al., Cytotoxicity of ascorbate, lipoic acid, and other antioxidants in hollow fibre in vitro tumours, British Journal of Cancer, vol. 84, No. 11, pp. 1544-1550, 2001.

Chamras et al., Fatty acid modulation of MCF-7 human breast cancer cell proliferation, apoptosis and differentiation, The Journal of Nutritional Biochemistry, vol. 13, No. 12, pp. 711-716, 2002.

Dechsupa et al., Quercetin, Siamois 1 and Siamois 2 induce apoptosis in human breast cancer MDA-mB-435 cells xenograft in vivo, Cancer Biology & Therapy, vol. 6, No. 1, pp. 56-61, 2007.

Fischer et al., Chemotherapeutic selectivity conferred by selenium: a role for p53-dependent DNA repair, Molecular Cancer Therapeutics, vol. 6, No. 1, pp. 355-361, 2007.

Hu et al., The protective role of selenium on the toxicity of cisplatin-contained chemotherapy regimen in cancer patients, Biol Trace Elem Res. Mar. 1997;56(3):331-41.

Idnap et al., Quercetin: Antitumor activity and pharmacological manipulations for increased therapeutic gains, Indian J Pharm Sci,2006, 68 (4): 465-469.

Jaakkola et al., Treatment with antioxidant and other nutrients in combination with chemotherapy and irradiation in patients with small-cell lung cancer, Anticancer Res. May.-Jun. 1992;12(3):599-606.

Jamison et al., Evaluation of the in vitro and in vivo antitumor activities of vitamin C and K-3 combinations against human prostate cancer, The Journal of Nutrition, vol. 131, No. 1, pp. 1585-160S, 2001.

Kandaswami et al., Ascorbic acid-enhanced antiproliferative effect of flavonoids on squamous cell carcinoma in vitro, Anticancer Drugs. Feb. 1993;4(1):91-6.

Kim et al., Se-methylselenocysteine induces apoptosis through caspase activation in HL-60 cells, Carcinogensis, vol. 22, No. 4, pp. 559-565, 2001.

Ledesma et al., Selenium and vitamin E for prostate cancer: post-SELECT (Selenium and Vitamin E Cancer Prevention Trial) status, Molecular Medicine, vol. 17, No. 1-2, pp. 134-143, 2011.

Ma et al., 1alpha,25-Dihydroxyvitamin D3 potentiates cisplatin antitumor activity by p73 induction in a squamous cell carcinoma model, Molecular Cancer Therapeutics, vol. 7, No. 9, pp. 3047-3055, 2008.

Ma et al., Reduction of CWR22 prostate tumor xenograft growth by combined tamoxifen-quercetin treatment is associated with inhibition of angiogenesis and cellular proliferation, Int J Oncol. May 2004;24(5):1297-304.

Markman, The Role of CA-125 in the Management of Ovarian Cancer, the Oncologist, 1997; 2:6-9.

McGuire et al., Vitamin D(3)-induced apoptosis of murine squamous cell carcinoma cells. Selective induction of caspase-dependent MEK cleavage and up-regulation of MEKK-1, The Journal of Biological Chemistry, vol. 276, No. 28, pp. 26365-26367, 2001.

Nicol et al., The effects of cyclophosphamide alone and in combination with ascorbic acid against murine ascites Dalton's lymphoma, Indian Journal of Pharmacology, vol. 38, No. 4, pp. 260-265 (2006).

Pathak et al., Potentiation of the Effect of Paclitaxel and Carboplatin by Antioxidant Mixture on Human Lung Cancer H520 Cells, Journal of the American College of Nutrition, vol. 21, No. 5, pp. 416-421 (2002).

Pelz et al., A new survival model for hyperthermic intraperitoneal chemotherapy (HIPEC) in tumor-bearing rats in the treatment of peritoneal carcinomatosis, BMC Cancer, vol. 5, p. 56, 2005.

Priego et al., Natural polyphenols facilitate elimination of HT-29 colorectal cancer xenografts by chemoradiotherapy: a Bcl-2- and superoxide dismutase 2-dependent mechanism, Mol Cancer Ther. Oct. 2008;7(10):3330-42.

Reddy et al., Vitamin C Augments Chemotherapeutic Response of Cervical Carcinoma HeLa Cells by Stabilizing P53, Biochemical and Biophysical Research Communications, vol. 282, No. 2, pp. 409-415 (2001).

Shlemkevich et al., -Fluorouracil combined with ascorbic acid in the treatment of patients with extensive gastric cancer, Vrachebnoe Delo, vol. No. 7, pp. 30-32 (1984). (English language summary listed on p. 32).

Van Der Woude et al., Biphasic modulation of cell proliferation by quercetin at concentrations physiologically relevant in humans, Cancer Letters, vol. 200, Issue 1, Oct. 8, 2003, pp. 41-47.

\* cited by examiner

Mitomycin C Killing Curve on HCT-116 cells. Cells were treated with vavious concentrations of Mitomycin C for three days. Cell viability was measured using MTS assay.

Cisplatin killing curve on HCT-116 cells. Cells were treated with vavious concentrations of Cisplatin. Cell viability was measured after three days using MTS assay.

FIGURE 2a

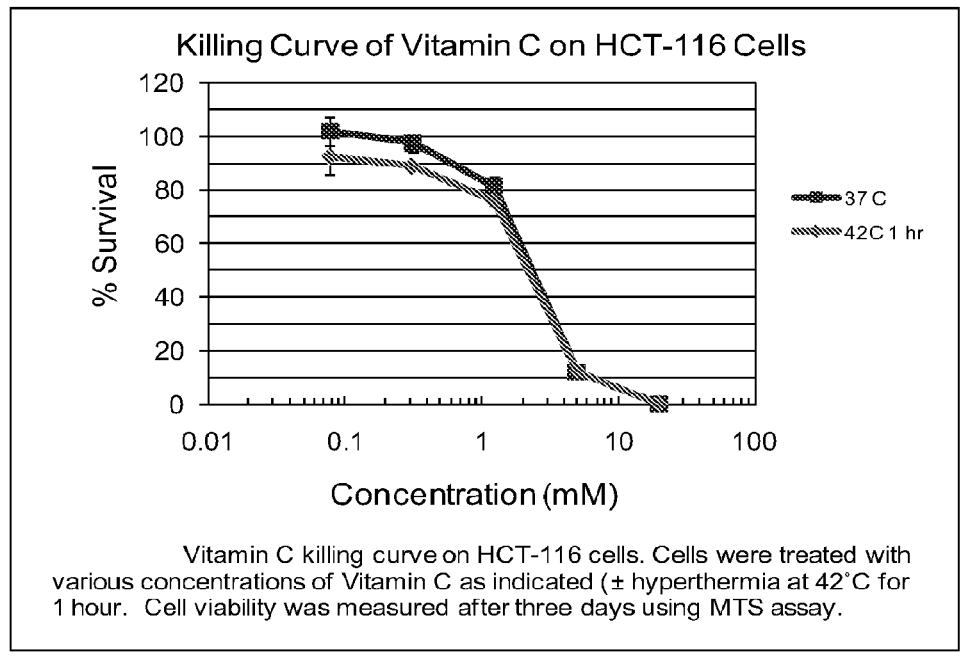

Vitamin C killing curve on HCT-116 cells. Cells were treated with various concentrations of Vitamin C as indicated (± hyperthermia at 42°C for 1 hour. Cell viability was measured after three days using MTS assay.

FIGURE 2b

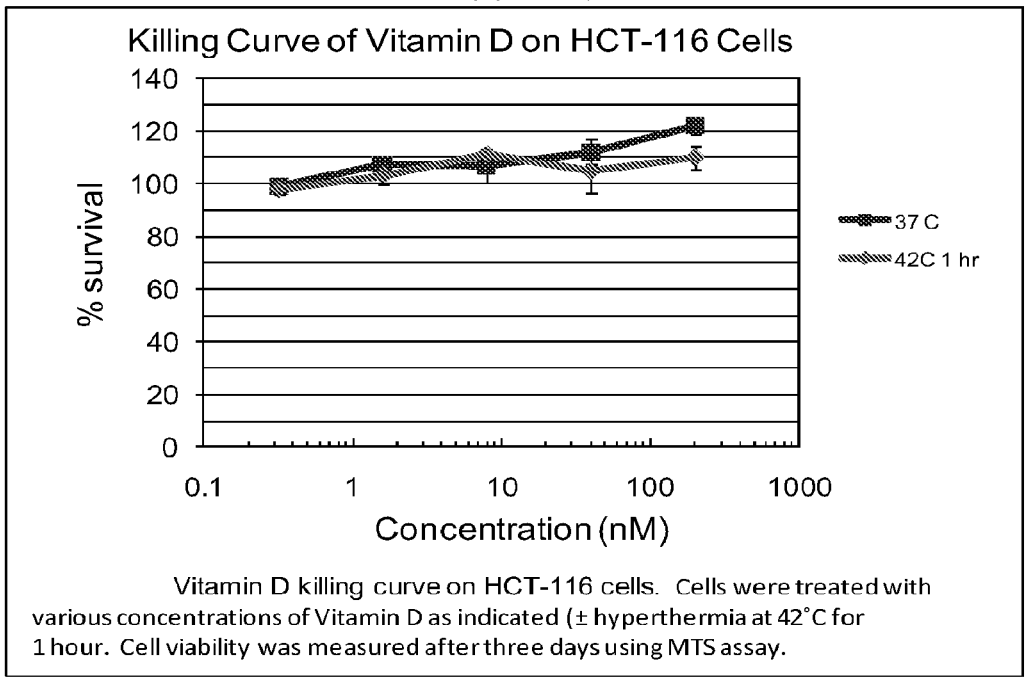

Vitamin D killing curve on HCT-116 cells. Cells were treated with various concentrations of Vitamin D as indicated (± hyperthermia at 42°C for 1 hour. Cell viability was measured after three days using MTS assay.

Figure 2c

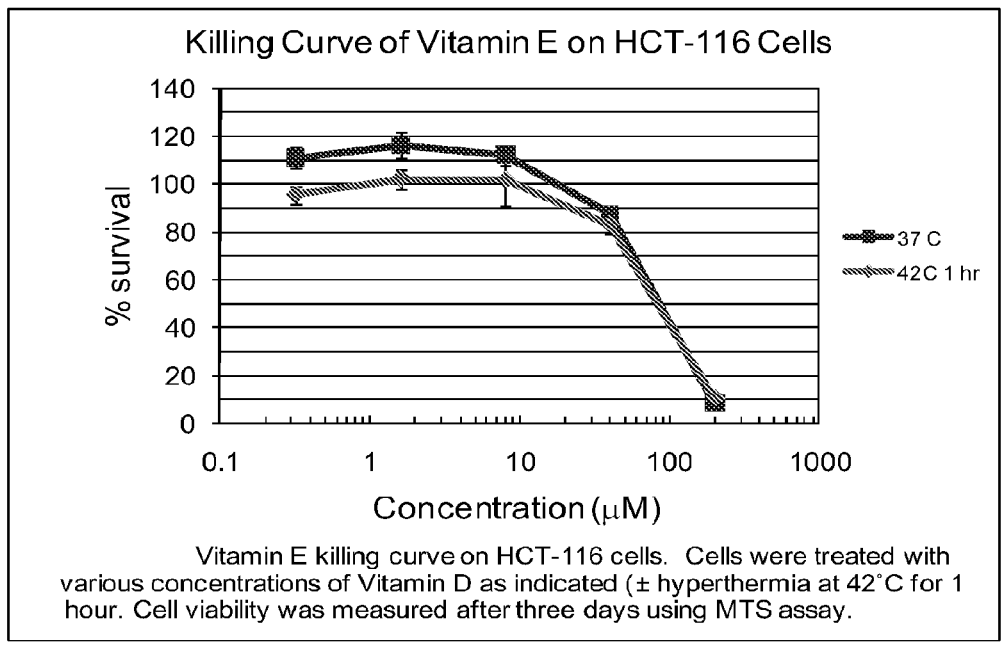

Vitamin E killing curve on HCT-116 cells. Cells were treated with various concentrations of Vitamin D as indicated (± hyperthermia at 42°C for 1 hour. Cell viability was measured after three days using MTS assay.

FIGURE 2d

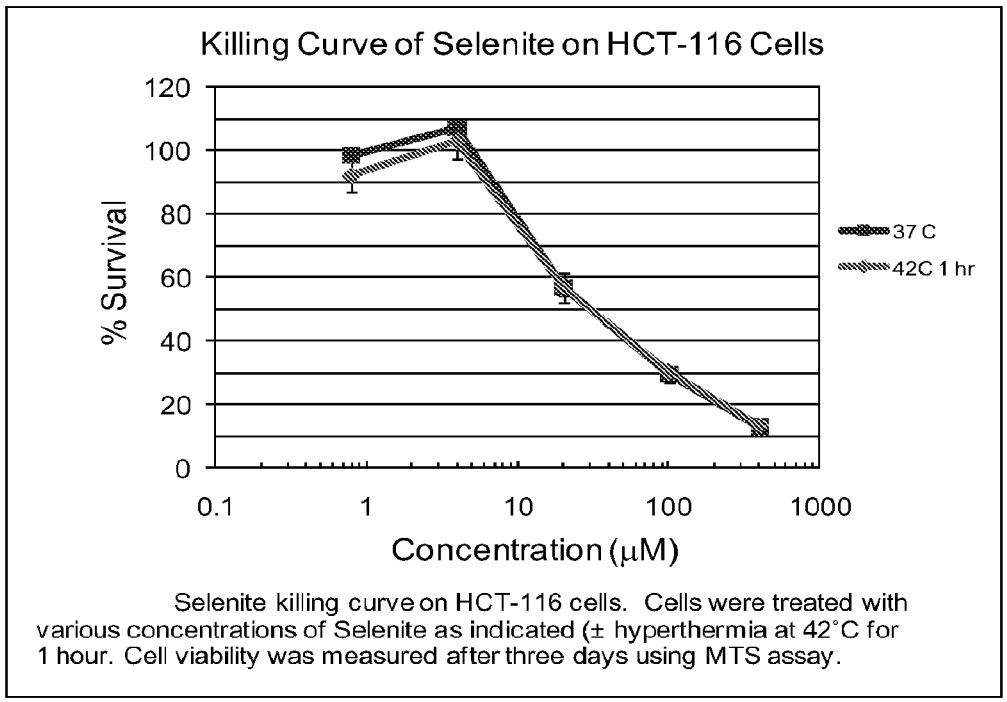

Selenite killing curve on HCT-116 cells. Cells were treated with various concentrations of Selenite as indicated (± hyperthermia at 42°C for 1 hour. Cell viability was measured after three days using MTS assay.

Cytotoxic effect of combination treatment with non-chemo agents on HCT-116 cells. Cells were treated with combinations of non-chemo agents as indicated (± hyperthermia at 42°C for 1 hour). Cell viability was measured after three days using MTS assay.

Cytotoxic effect of combination treatment with mitomycin C and non-chemo agents on HCT-116 cells. Cells were treated with combinations of two concentrations of Mitomycin C and non-chemo agents as indicated (± hyperthermia at 42°C for 1 hour). Cell viability was measured after three days using MTS assay.

Cytotoxic effect of combination treatment with Cisplatin and non-chemo agents on HCT-116 cells. Cells were treated with combinations of two concentrations of Cisplatin and non-chemo agents as indicated (± hyperthermia at 42°C for 1 hour). Cell viability was measured after three days using MTS assay.

Cytotoxic effect of combination treatment with non-chemo agents on HCT-116 cells. Cells were treated with combinations of non-chemo agents as indicated (± hyperthermia at 42°C for 1 hour). Cell viability was measured after three days using MTS assay.

Cytotoxic effect of combination treatment with mitomycin C and non-chemo agents on HCT-116 cells. Cells were treated with combinations of two concentrations of Mitomycin C and non-chemo agents as indicated (± hyperthermia at 42°C for 1 hour). Cell viability was measured after three days using MTS assay.

Cytotoxic effect of combination treatment with Cisplatin and non-chemo agents on HCT-116 cells. Cells were treated with combinations of two concentrations of Cisplatin and non-chemo agents as indicated (± hyperthermia at 42°C for 1 hour). Cell viability was measured after three days using MTS assay.

Cytotoxic effect of combination treatments with chemo and non-chemo agents on HCT-116 cells. Cells were treated with combinations of chemo and non-chemo agents as indicated (± hyperthermia at 42°C for 1 hour). Cell viability was measured after three days using MTS assay.

Cytotoxic effect of combination treatment with non-chemo agents on HCT-116 cells. Cells were treated with combinations of non-chemo agents as indicated (± hyperthermia at 42°C for 1 hour). Cell viability was measured after three days using MTS assay.

Cytotoxic effect of combination treatments with chemo and non-chemo agents on HCT-116 cells. Cells were treated with combinations of chemo and non-chemo agents as indicated (± hyperthermia at 42°C for 1 hour). Cell viability was measured after three days using MTS assay.

Cytotoxic effect of combination treatments with chemo and non-chemo agents on HCT-116 cells. Cells were treated with combinations of chemo and non-chemo agents as indicated (± hyperthermia at 42°C for 1 hour). Cell viability was measured after three days using MTS assay.

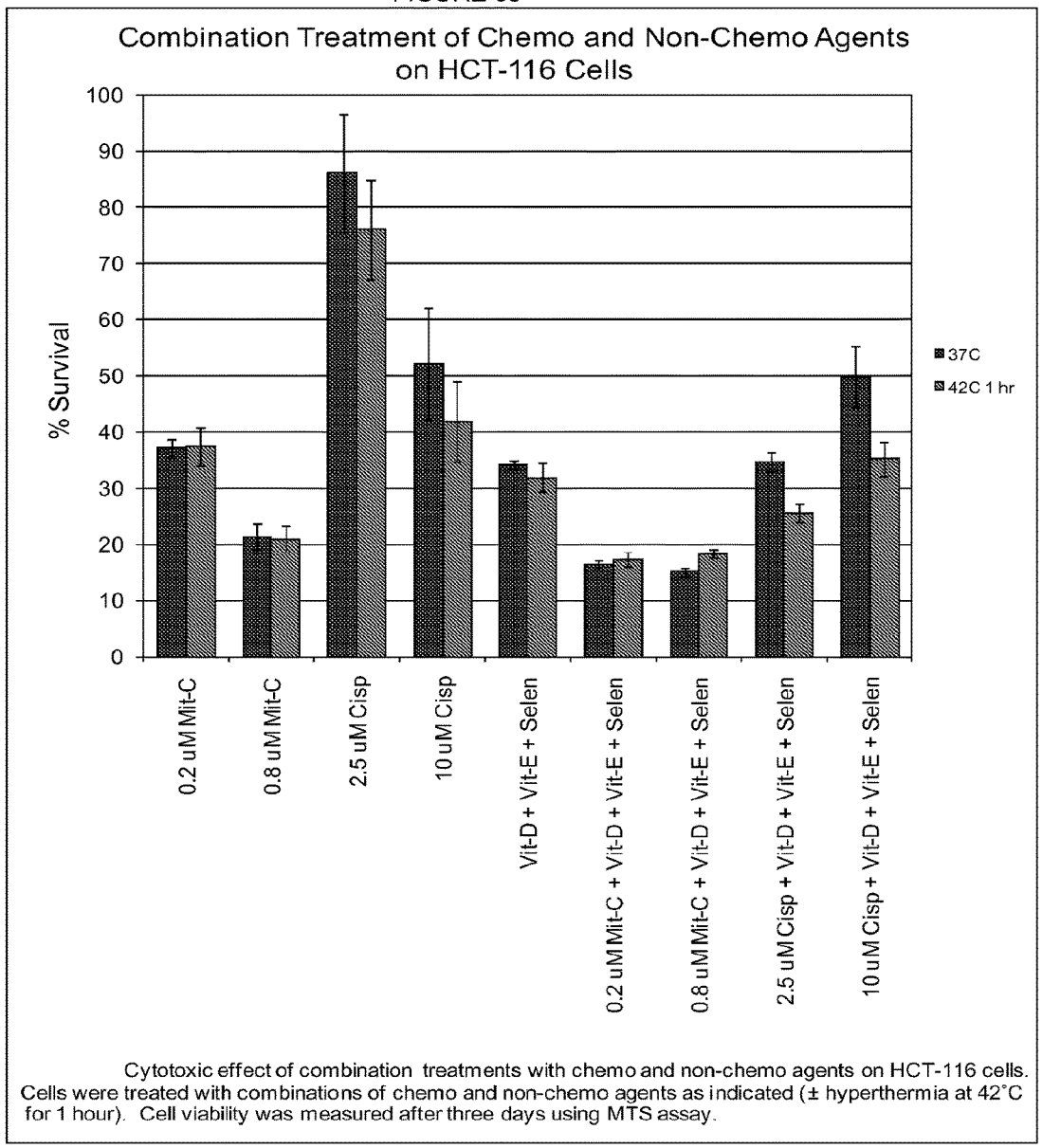

Cytotoxic effect of combination treatment with non-chemo agents on HCT-116 cells. Cells were treated with combinations of non-chemo agents as indicated (± hyperthermia at 42°C for 1 hour). Cell viability was measured after three days using MTS assay.

Cytotoxic effect of combination treatment on HCT-116 cells. HCT-116 cells were treated with combinations of chemo and non-chemo agents as indicated (± hyperthermia at 42°C for 2 hour). Cell viability was measured using MTS assay immediately after the treatment.

COMPOSITIONS AND METHODS FOR ENHANCING THE EFFECTIVENESS OF SYSTEMIC, HIPEC, IP, AND RELATED CANCER TREATMENTS

CROSS-REFERENCE TO RELATED APPLICATIONS

This application is divisional of U.S. patent application Ser. No. 13/812,120 filed Mar. 12, 2013, which application is a 371 application of International Patent Application No. PCT/US2011/045247 filed Jul. 25, 2011, which application claims priority to the filing date of U.S. Provisional Patent Application Ser. No. 61/367,820 filed on Jul. 26, 2010, pursuant to 35 U.S.C. § 119 (e); the disclosure of which applications are herein incorporated by reference.

INTRODUCTION

Field of the Invention

Aspects of the invention are directed to administration of a composition comprising one or more generally regarded as safe (GRAS) compounds selected from the group of components consisting of vitamins, selenium, fatty acids, fatty acid salts, and fatty acid esters, or their pharmaceutically acceptable salts to enhance the effectiveness of chemotherapeutic agents with or without concomitant hyperthermia treatment.

Aspects of the invention relate to a method of treating hyper-proliferative diseases, such as cancer. Methods of interest use a composition comprising one or more generally regarded as safe (GRAS) compounds selected from the group of components consisting of vitamins, selenium, fatty acids, fatty acid salts, and fatty acid esters, or their pharmaceutically acceptable salts either alone, or in combination with chemotherapeutic agents to kill target hyperproliferative, e.g., cancerous, cells.

Background

The treatment of human cancer with chemotherapeutic agents has been long practiced, with varying degrees of success. There remains an acute need to be able to discover agents that can be administered in conjunction with chemotherapeutic agents to increase the effectiveness of the latter.

The peritoneum is the inner lining found throughout the abdominal cavity. Cancer cells can spread into the peritoneum from tumors originally located in the colon, pancreas, appendices, gastrointestinal tract, ovaries, and other organs. Typically, when cancerous cells have spread (metastasized) from one location to another, doctors will prescribe systemic chemotherapeutic compounds by injection into a patient's bloodstream. The goal of such methods is to destroy wayward cancer cells by basically saturating a patient's body with chemical poisons. This is effective for a number of metastatic cancers. However, such methods are far less effective for peritoneal cancers, due to the fact that the abdominal lining naturally has significantly less blood flow than other tissues in the body, thus creating what is known in the art as a "peritoneal barrier".

Accordingly, the penetration of chemotherapeutic chemicals into the peritoneal cavity is very low. Reacting to this challenge, medical researchers developed a procedure called intraperitoneal hyperthermic chemo-perfusion or "HIPEC". Immediately following tumor debulking surgery a surgeon can administer the HIPEC procedure by inserting tubing into the abdomen and circulating approximately three liters of sterile solution throughout the abdominal cavity. The solution is heated to approximately 42 C (107.6 F) and then chemotherapeutic agents are added. This heated chemotherapy solution is circulated throughout the abdominal cavity for approximately 90 minutes to 2 hours. After this time period the solution is drained and the abdominal cavity is rinsed.

HIPEC delivers what systemic administration cannot—the direct contact of anti-cancer compounds to the cancerous cells found within the peritoneal area. Researchers discovered that heating the circulating chemotherapy solution further increased their ability to kill cancer cells in the patient's abdomen. The use of HIPEC is expanding, worldwide.

Another procedure, called "IP Therapy", oftentimes used to treat ovarian cancer, is similar to HIPEC, namely, chemotherapy is delivered directly to tumors confined to the peritoneal cavity through abdominal access ports installed through the skin surface. However, heat is not typically used, and the solution is not circulated but left in the abdominal cavity to be absorbed. This method is used to treat ovarian cancer. Generally, six cycles of chemotherapy solution are administered, once every three weeks.

The current carrier solutions used in the art generally consist of Lactated Ringers (LR)—which is used for HIPEC, IP Therapy, and related therapies. LR is sterile water with trace amounts of sodium chloride, potassium chloride, and calcium chloride. LR is used throughout the hospital for IV electrolyte balancing; its use in HIPEC, IP Therapy, and related therapies is as a carrier for heat and chemotherapy.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

SUMMARY

We have now discovered that a composition comprising one or more generally regarded as safe (GRAS) compounds selected from the group of components consisting of vitamins, selenium, fatty acids, fatty acid salts, and fatty acid esters, or their pharmaceutically acceptable salts can exert significant cancer cell killing properties. The discovered compositions also demonstrate significant increases in the cancer cell killing effectiveness of chemotherapeutic compounds typically used during HIPEC, IP, and related therapies.

Accordingly, aspects of the invention provide new compositions of GRAS compounds for cancer treatments, as well as compositions that significantly elevate the cancer-killing abilities of chemotherapeutic agents. The instant inventors have found that new carrier solutions can be formulated that significantly enhance the cancer killing ability for systemic treatments, HIPEC, IP Therapy, and related procedures by incorporating various "helper" chemical compounds. To this end, we have developed proprietary solutions that contain select compounds aimed at potentiating the lethality of standard chemotherapeutic agents.

Accordingly, the instant invention details the development of a potent cancer-killing formulations that can be used in HIPEC, IP Therapy, and related therapies, as well as systemically, to significantly enhance efficacy and patient outcome.

Methods for treating cancers, tumors, and neoplasms using a composition comprising one or more generally regarded as safe (GRAS) compounds selected from the group of components consisting of vitamins, selenium, fatty acids, fatty acid salts, and fatty acid esters, and mixtures of two or more said components, either as a stand-alone treatment or in combination with one or more anti-cancer drugs or devices or other anti-neoplastic agents, treatments, or devices are provided. In some instances, concomitant hyperthermia therapy is employed. Also provided are compositions and kits containing the compositions, for implementation of various aspects of the invention.

Aspects of the invention are directed to administration of a composition comprising one or more generally regarded as safe (GRAS) compounds selected from the group of components consisting of vitamins, selenium, fatty acids, fatty acid salts, and fatty acid esters to kill cancer cells as a stand-alone therapy as well as to enhance the effectiveness of anti-cancer therapies with chemotherapeutic agents with or without concomitant hyperthermia treatment. In a specific example, administration of a composition comprising one or more generally regarded as safe (GRAS) compounds selected from the group of components consisting of vitamins, selenium, fatty acids, fatty acid salts, and fatty acid esters, in conjunction with cisplatin, cisplatin-based therapies, carboplatin, mitomycin, vincristine, methotrexate, fluorouracil, calcium folinate, cytosine arabinoside, cyclophosphamide, epirubicin, etoposide, bleomycin A5, taxanes, mitoxanthrone, cylcophosphamide, topoisomerase inhibitors, angiogenesis inhibitors, cisplatin-based therapies, differentiation agents, signal transduction inhibitors, busulfan, doxorubicin rapid dissolution, etoposide, 5-fluorouracil, tamoxifen, or combinations thereof, results in a significant increase in tumor cell death compared to cisplatin, cisplatin-based therapies, carboplatin, mitomycin, vincristine, methotrexate, fluorouracil, calcium folinate, cytosine arabinoside, cyclophosphamide, epirubicin, etoposide, bleomycin A5, taxanes, mitoxanthrone, cylcophosphamide, topoisomerase inhibitors, angiogenesis inhibitors, cisplatin-based therapies, differentiation agents, signal transduction inhibitors, busulfan, doxorubicin rapid dissolution, etoposide, 5-fluorouracil, tamoxifen, or combinations thereof, administration alone.

Methods of treating systemically metastasized, peritoneal, colorectal, gastric, ovarian, appendiceal, pseudomyxoma, sarcoma, peritoneal mesothelioma, and others cancers are disclosed. Also disclosed are methods of treating cancers that have migrated into the abdominal cavity. The methods comprise administering to a patient a therapeutically effective amount of a composition comprising one or more generally regarded as safe (GRAS) compounds selected from the group of components consisting of vitamins, selenium, fatty acids, fatty acid salts, and fatty acid esters, and pharmaceutically acceptable salts thereof.

Aspects of the invention include methods of killing cancer cells and of sensitizing cancer cells to make them more susceptible to anti-cancer agents, which involves administering to a patient an effective amount of a composition comprising one or more generally regarded as safe (GRAS) compounds selected from the group of components consisting of vitamins, selenium, fatty acids, fatty acid salts, and fatty acid esters, or their pharmaceutically acceptable salts.

Aspects of the invention include compositions for killing cancer cells and methods for sensitizing cancer therapies. The invention provides such compositions comprising a composition comprising one or more generally regarded as safe (GRAS) compounds selected from the group of components consisting of vitamins, selenium, fatty acids, fatty acid salts, and fatty acid esters. The compositions and methods of the invention are useful in in vitro study of cancer therapy resistance, as well as ex vivo and in vivo therapy of cancer.

Various embodiments of the invention include, but are not limited to:
1. A method for killing cancer cells of a mammal comprising: contacting the cancer cells in vitro with one or more compounds selected from the group of Vitamin C, Selenium, or Quercetin; determining whether the cancer cells are affected in vitro by one or more compounds selected from the group of Vitamin C, Selenium, or Quercetin, and, if so; administering one or more compounds selected from the group of Vitamin C, Selenium, or Quercetin to the cancer cells of the mammal in vivo in an amount effective to kill cancer cells.

2. A method for sensitizing cancer cells of a mammal to a therapeutic treatment comprising: contacting the cancer cells in vitro with one or more compounds selected from the group of Vitamin C, Selenium, or Quercetin; determining whether the cancer cells are sensitized in vitro to a therapeutic treatment by one or more compounds selected from the group of Vitamin C, Selenium, or Quercetin, and, if so; administering one or more compounds selected from the group of Vitamin C, Selenium, or Quercetin to the cancer cells of the mammal in vivo in an amount effective to sensitize the cancer cells to the therapeutic treatment.

3. The method of embodiment 2, wherein the therapeutic treatment is chemotherapy and comprises the administration of an effective amount of a chemotherapeutic agent to the mammal.

4. The method of embodiment 1 or 2, wherein the therapeutic treatment is chemotherapy combined with hyperthermic therapy.

5. The method of embodiment 1 or 2, wherein the therapeutic treatment is chemotherapy, radiation therapy, biological therapy, photodynamic therapy, hyperthermic therapy or combinations thereof.

6. A method of screening for an agent useful for sensitizing a cancer cell to chemotherapeutic damage by a second agent, which comprises: (i) contacting a tumor cell line with a chemotherapeutic agent and a test agent selected from one or more compounds selected from the group of Vitamin C, Selenium, or Quercetin, (ii) detecting the amount of tumor cell death; and (iii) selecting the test agent that increases the tumor cell death as an agent useful for sensitizing a cancer cell to chemotherapeutic damage by the second agent; wherein the control is the amount of tumor cell death in the absence of the test agent.

7. A method for treating a mammal diagnosed with cancer comprising: administering to the mammal the therapeutic treatment and an amount of one or more compounds selected from the group of Vitamin C, Selenium, or Quercetin effective to sensitize the cancer cells to the therapeutic treatment.

8. The method of embodiment 7, wherein the therapeutic treatment is chemotherapy and comprises the administration of an effective amount of a chemotherapeutic agent to the mammal.

9. The method of embodiment 7, wherein the therapeutic treatment is chemotherapy combined with hyperthermic therapy.

10. The method of embodiment 7, wherein the therapeutic treatment is chemotherapy, radiation therapy, biological therapy, photodynamic therapy, hyperthermic therapy, immunotherapy or combinations thereof.

11. A method of treating a cancer comprising administering to a subject in need thereof an effective amount of a composition comprising one or more compounds selected from the group of Vitamin C, Selenium, or Quercetin, and pharmaceutically acceptable salts thereof, wherein said cancer is selected from the group consisting of systemic metastases, peritoneal, colorectal, gastric, ovarian, appendiceal, pseudomyxoma, sarcoma, and peritoneal mesothelioma.

12. The method of embodiment 11, further comprising surgery, radiation therapy, chemotherapy, gene therapy, immunotherapy, or a combination thereof.

13. The method of embodiment 11, wherein a tumor cell undergoes apoptosis, cell cycle arrest, and/or necrosis in said subject.

14. A method for killing tumor cells in a warm-blooded animal, the method comprising: administering to the warm-blooded animal a composition comprising one or more compounds selected from the group of Vitamin C, Selenium, or Quercetin in an amount effective to sensitize the tumor cells.

15. A method for killing tumor cells in a warm-blooded animal, the method comprising:
(a) administering to the warm-blooded animal the composition comprising one or more compounds selected from the group of Vitamin C, Selenium, or Quercetin in an amount effective to sensitize the tumor cells; and
(b) after a time interval sufficient to enhance chemosensitization of the tumor cells, contacting the tumor cells with a dose of chemotherapy effective to kill the tumor cells.

16. A method for treating the peritoneal area of a warm-blooded animal which is afflicted by cancer, the method comprising applying the compounds or salt of one or more compounds selected from the group of Vitamin C, Selenium, or Quercetin to the afflicted area.

17. A method for killing cancer cells in a cancer patient comprising administering to said cancer patient (i) an effective amount of a chemotherapeutic agent, and (ii) an effective amount of a composition comprising one or more generally regarded as safe (GRAS) compound selected from the group of components consisting of vitamins, selenium, fatty acids, fatty acid salts, and fatty acid esters, or their pharmaceutically acceptable salt, wherein the administration of (i) said chemotherapeutic agent and (ii) said composition comprising one or more generally regarded as safe (GRAS) compounds selected from the group of components consisting of vitamins, selenium, fatty acids, fatty acid salts, and fatty acid esters, or their pharmaceutically acceptable salt is effected jointly or sequentially, and wherein the amount of said chemotherapeutic agent and said a composition comprising one or more generally regarded as safe (GRAS) compounds selected from the group of components consisting of vitamins, selenium, fatty acids, fatty acid salts, and fatty acid esters, or their pharmaceutically acceptable salt is effective to killing cancer cells which are contained in said patient, and further wherein the amount of said composition comprising one or more generally regarded as safe (GRAS) compounds selected from the group of components consisting of vitamins, selenium, fatty acids, fatty acid salts, and fatty acid esters, or their pharmaceutically acceptable salt is sufficient to sensitize said cancer cells which are contained in said patient such that greater numbers of said cancer cells are killed in comparison to when either said chemotherapeutic agent or said composition comprising one or more generally regarded as safe (GRAS) compounds selected from the group of components consisting of vitamins, selenium, fatty acids, fatty acid salts, and fatty acid esters, or their pharmaceutically acceptable salt are administered singularly.

18. A method for treating a subject having a tumor located in the intraperitoneal cavity, comprising administering to a subject having a tumor located in the intraperitoneal cavity an amount of one or more compounds selected from the group of Vitamin C, Selenium, or Quercetin sufficient to increase tumor cell killing and a therapeutically effective amount of an chemotherapeutic agent, wherein the subject is a mammal, the tumor is a systemic metastases, peritoneal, colorectal, gastric, ovarian, appendiceal, pseudomyxoma, sarcoma, or peritoneal mesothelioma, and the chemotherapeutic agent is more toxic to a tumor cell than to a tumor cell not contacted with one or more compounds selected from the group of Vitamin C, Selenium, or Quercetin.

19. A method of synergistically inhibiting the growth of human cancer cells, comprising contacting the cells with a first composition which comprises an agent selected from one or more generally regarded as safe (GRAS) compounds selected from the group of components consisting of vitamins, selenium, fatty acids, fatty acid salts, and fatty acid esters, or their pharmaceutically acceptable salt are administered singularlyand a second composition which comprises an agent selected from the group consisting of cisplatin, cisplatin-based therapies, carboplatin, mitomycin, vincristine, methotrexate, fluorouracil, calcium folinate, cytosine arabinoside, cyclophosphamide, epirubicin, etoposide, bleomycin A5, taxanes, mitoxanthrone, cylcophosphamide, topoisomerase inhibitors, angiogenesis inhibitors, cisplatin-based therapies, differentiation agents, signal transduction inhibitors, busulfan, doxorubicin rapid dissolution, etoposide, 5-fluorouracil, tamoxifen, or combinations thereof.

20. The method of embodiment 19, wherein the agent is doxorubicin.

21. The method of embodiment 19 wherein the agent is cisplatin.

22. The method of embodiment 19 wherein the agent is paclitaxel.

23. The method of embodiment 19, wherein the first and second compositions are administered to a human cancer patient.

24. The method of embodiment 23 wherein the first and second compositions are co-administered.

25. The method of embodiment 23 wherein the first and second compositions are administered in an episodic regimen.

26. A method of treating a cancer in a mammal, comprising administering an effective amount of a combined therapeutic agent, wherein the combined therapeutic agent comprises: a) an agent selected from one or more generally regarded as safe (GRAS) compounds selected from the group of components consisting of vitamins, selenium, fatty acids, fatty acid salts, and fatty acid esters, or their pharmaceutically acceptable salt are administered singularly; and c) a chemical drug.

27. The method of embodiment 26, wherein the one or more compounds selected from the group of Vitamin C, Selenium, or Quercetin and chemical drug are formulated in a single pharmaceutical composition, or each is formulated in a separate pharmaceutical composition.

28. The method of embodiment 26, wherein the chemical drug is selected from the group consisting of: cisplatin, cisplatin-based therapies, carboplatin, mitomycin, vincristine, methotrexate, fluorouracil, calcium folinate, cytosine arabinoside, cyclophosphamide, epirubicin, etoposide, bleomycin A5, taxanes, mitoxanthrone, cylcophosphamide, topoisomerase inhibitors, angiogenesis inhibitors, cisplatin-based therapies, differentiation agents, signal transduction inhibitors, busulfan, doxorubicin rapid dissolution, etoposide, 5-fluorouracil, tamoxifen, or combinations thereof.

29. A pharmaceutical composition for treating a subject having a tumor comprising an amount of one or more compounds selected from the group of Vitamin C, Selenium, or Quercetin sufficient to kill tumor cells.

30. A pharmaceutical composition for treating a subject having a tumor comprising an amount of a chemotherapeutic agent and one or more compounds selected from the group of Vitamin C, Selenium, or Quercetin sufficient to kill tumor cells; and a pharmaceutically acceptable carrier.

31. A combination, comprising: a) one or more compounds selected from the group of Vitamin C, Selenium, or Quercetin and b) a chemical drug.

32. The combination of embodiment 31, wherein the one or more compounds selected from the group of Vitamin C, Selenium, or Quercetin and chemical drug are formulated in a single pharmaceutical composition, or each is formulated in a separate pharmaceutical composition.

33. The combination of embodiment 31, wherein said chemical drug is selected from the group consisting of cisplatin, cisplatin-based therapies, carboplatin, mitomycin, vincristine, methotrexate, fluorouracil, calcium folinate, cytosine arabinoside, cyclophosphamide, epirubicin, etoposide, bleomycin A5, taxanes, mitoxanthrone, cylcophosphamide, topoisomerase inhibitors, angiogenesis inhibitors, cisplatin-based therapies, differentiation agents, signal transduction inhibitors, busulfan, doxorubicin rapid dissolution, etoposide, 5-fluorouracil, and tamoxifen, or combinations thereof.

34. The combination of embodiment 31, further comprising an anti-neoplasm agent.

35. The combination of embodiment 31, further comprising a facilitating agent that facilitates conjugation between the chemical drug and the one or more compounds selected from the group of Vitamin C, Selenium, or Quercetin.

36. A kit comprising the combination of embodiment 31.

37. An article of manufacture, comprising: a) packaging material; b) the combination of embodiment 31; and c) a label indicating that the article is for treating cancer.

38. A combination, comprising: a) one or more compounds selected from the group of Vitamin C, Selenium, or Quercetin, and b) a chemical drug.

39. The combination of embodiment 38, wherein the one or more compounds selected from the group of Vitamin C, Selenium, or Quercetin and chemical drug are formulated in a single pharmaceutical composition, or each is formulated in a separate pharmaceutical composition.

40. The combination of claim embodiment 38, wherein said chemical drug is selected from the group consisting of cisplatin, cisplatin-based therapies, carboplatin, mitomycin, vincristine, methotrexate, fluorouracil, calcium folinate, cytosine arabinoside, cyclophosphamide, epirubicin, etoposide, bleomycin A5, taxanes, mitoxanthrone, cylcophosphamide, topoisomerase inhibitors, angiogenesis inhibitors, cisplatin-based therapies, differentiation agents, signal transduction inhibitors, busulfan, doxorubicin rapid dissolution, etoposide, 5-fluorouracil, and tamoxifen, or combinations thereof.

41. The combination of embodiment 38, further comprising an anti-neoplasm agent.

42. The combination of embodiment 38, further comprising a facilitating agent that facilitates conjugation between the chemical drug and the one or more compounds selected from the group of Vitamin C, Selenium, or Quercetin.

43. A kit comprising the combination of embodiment 38.

44. An article of manufacture, comprising: a) packaging material; b) the combination of embodiment 38; and c) a label indicating that the article is for treating cancer.

45. A dialysate composition for use in hemodialysis, comprising:
a suspension including a chemotherapeutic compound and one or more compounds selected from the group of Vitamin C, Selenium, or Quercetin.

46. The composition of embodiment 45 wherein the compound is Vitamin C.
47. The composition of embodiment 45 wherein the compound is Selenium.
48. The composition of embodiment 45 wherein the compound is Quercetin.
49. A dialysate composition for use in hemodialysis, comprising:
a suspension including a chemotherapeutic compound, one or more compounds selected from the group of Vitamin C, Selenium, or Quercetin, and a surfactant.
50. A composition for treatment of cancer located in the peritoneum comprising:
an aqueous suspension comprising a chemotherapeutic compound and one or more compounds selected from the group of Vitamin C, Selenium, or Quercetin.
51. A composition for treatment of cancer located in the peritoneum comprising:
an aqueous suspension comprising a chemotherapeutic compound, one or more compounds selected from the group of Vitamin C, Selenium, or Quercetin, and a surfactant.

DEFINITIONS

Figure 1A:
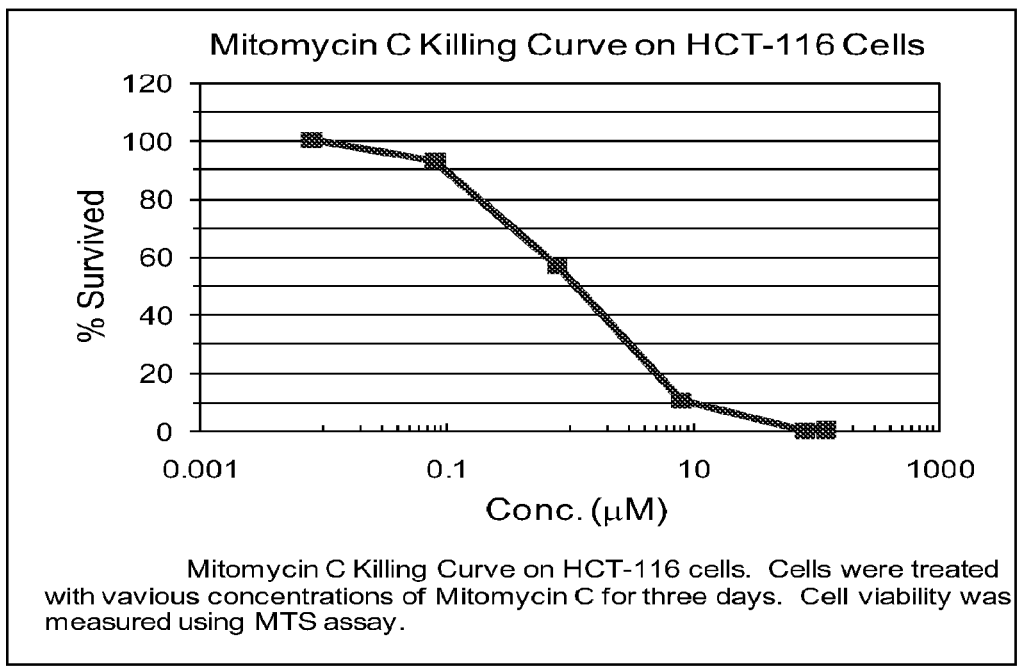
FIGS. 1a to 8 provide graphical results of obtained as reported in the Experimental Section, below.

Unless defined otherwise, all technical and scientific terms used herein have the same meaning as is commonly understood by one of ordinary skill in the art to which this invention belongs.

As used herein Vitamin C, Selenium, and Quercetin includes any compound chemical related to such designations, such as analogues and derivatives thereof, including but not limited to: solvated variants, hydrated versions, isomers, racemic mixtures, salts, etc.

As used herein, chemotherapeutic agent or chemotherapeutic compound means any agent or compound used in the art for the treatment of cancer. Chemotherapy can be conducted with a host of agents, and can include, among a vast array of agents: cisplatin, cisplatin-based compounds, carboplatin, mitomycin, vincristine, methotrexate, fluorouracil, calcium folinate, cytosine arabinoside, cyclophosphamide, epirubicin, etoposide, bleomycin A5, taxanes, mitoxanthrone, cylcophosphamide, topoisomerase inhibitors, angiogenesis inhibitors, cisplatin-based therapies, differentiation agents, signal transduction inhibitors, busulfan, doxorubicin rapid dissolution, etoposide, 5-fluorouracil, tamoxifen, their salts, and combinations thereof.

As used herein, cancer refers to a general term for diseases caused by any type of tumor.

As used herein, an anti-cancer treatment refers to any treatment designed to treat the cancer, tumor, or neoplasm by lessening or ameliorating its symptoms. Treatments that prevent the occurrence of cancer, tumor, or neoplasm or lessen its severity are also contemplated.

As used herein, anti-cancer agent (or anti-neoplastic agent or anti-tumor agent) encompasses all agents and therapeutics modalities known to one of skill in the art to ameliorate the symptoms in some manner of a cancer, neoplasm, or tumor. These include any agents, used alone or in combination with other agents or compounds, can reduce, ameliorate, trigger a state of remission of symptoms or markers associated with cancers, tumors, and the like, and can be used in methods and compositions provided herein.

As used herein, neoplasm refers to abnormal new growth, and thus means the same as tumor, which may be benign or malignant.

By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the side-effects of the doxorubicin treatment or at least the symptoms that characterize the side-effects As used herein, hyperthermia and hyperthermic treatment refer to subjection of a body (or a least a portion thereof), to temperatures above 37° C., such as to temperature of 40° C. or more, including 41° C. or more, such as 42° C. or more, such as 40 to 45° C.; for a desired amount of time, e.g., 1 min or longer, e.g., 5 min or longer, including 10 minute or longer, e.g., 1 minute to 2 hours, such as 5 minutes to 1 hour.

DETAILED DESCRIPTION

Embodiments of the invention are based on the discovery that a composition comprising one or more generally regarded as safe (GRAS) compounds selected from the group of components consisting of vitamins, selenium, fatty acids, fatty acid salts, and fatty acid esters, or their pharmaceutically acceptable salts, can be used as a 1) stand-alone compositions useful for killing cancer cells and/or to sensitize cancer cells to other chemotherapeutic therapies.

Aspects of the invention include compositions with anticancer effects, and compositions for enhancing the anticancer effect of chemotherapeutic compounds. Embodiments of the invention include compositions and methods for directly killing cancerous cells and tissues, as well as sensitizing cancerous cells and tissues to other treatments such as chemotherapy. Compositions of interest include compositions comprising one or more generally regarded as safe (GRAS) compounds selected from the group of components consisting of vitamins (e.g., Vitamin C, Vitamin D, Vitamin E), selenium compounds (e.g., selenite), fatty acids, fatty acid salts, and fatty acid esters, flavanoids (e.g., quercetin) or their pharmaceutically acceptable salts, and a chemotherapy agent. Combinations of GRAS compounds of interest include, but are not limited to combinations of Vitamin C and another GRAS compound, e.g., combinations of Vitamin C and a selenium compound and/or a flavanoid, e.g., Vit-C/Selenite/Quercetin; Vit-C/Quercetin; and Vit-C/Selenite.

In another aspect, the present invention provides a method for in vivo sensitizing a mammal to a therapeutic treatment, the method comprising administrating to the mammal diagnosed with cancer an effective amount of a composition comprising one or more generally regarded as safe (GRAS) compounds selected from the group of components consisting of vitamins, selenium, fatty acids, fatty acid salts, and fatty acid esters, or their pharmaceutically acceptable salts.

Embodiments of the invention include methods for killing cancer cells in a subject stricken with cancer, the methods comprising: (1) obtaining a cancer sample from the mammal; (2) contacting the cancer sample with an effective amount of composition comprising one or more generally regarded as safe (GRAS) compound selected from the group of components consisting of vitamins, selenium, fatty acids, fatty acid salts, and fatty acid esters, or their pharmaceutically acceptable salts.

Aspects of the invention also include methods for ex vivo sensitizing a mammal diagnosed with cancer to a therapeutic treatment, the methods comprising: (1) obtaining a cancer sample from the mammal; (2) contacting the cancer sample with an effective amount of a composition comprising one or more generally regarded as safe (GRAS) compounds selected from the group of components consisting of vitamins, selenium, fatty acids, fatty acid salts, and fatty acid esters, or their pharmaceutically acceptable salts; and (3) returning the cancer sample after the contacting of (2) to the mammal.

Also provided are methods for sensitizing a cancer sample to a therapeutic treatment, the method comprising contacting the cancer sample with an effective amount of a composition comprising one or more generally regarded as safe (GRAS) compounds selected from the group of components consisting of vitamins, selenium, fatty acids, fatty acid salts, and fatty acid esters, or their pharmaceutically acceptable salts.

Also provided are methods of sensitizing cancer cells for systemic administration, HIPEC, IP, and related therapies which involves administering to a patient an effective amount of a composition comprising one or more generally regarded as safe (GRAS) compounds selected from the group of components consisting of vitamins, selenium, fatty acids, fatty acid salts, and fatty acid esters, or their pharmaceutically acceptable salts and chemotherapeutic agents either jointly or sequentially, wherein the chemotherapeutic agent or agents are selected from the group of cisplatin, cisplatin-based therapies, carboplatin, mitomycin, vincristine, methotrexate, fluorouracil, calcium folinate, cytosine arabinoside, cyclophosphamide, epirubicin, etoposide, bleomycin A5, taxanes, mitoxanthrone, cylcophosphamide, topoisomerase inhibitors, angiogenesis inhibitors, cisplatin-based therapies, differentiation agents, signal transduction inhibitors, busulfan, doxorubicin rapid dissolution, etoposide, 5-fluorouracil, tamoxifen, or combinations thereof.

Aspects of the invention further include methods of eliminating or reducing the hyperproliferative activity of human cancer or neoplastic cells. The method includes use of a composition comprising one or more generally regarded as safe (GRAS) compounds selected from the group of components consisting of vitamins, selenium, fatty acids, fatty acid salts, and fatty acid esters, or their pharmaceutically acceptable salts, with anticancer agents to additively or synergistically kill cancerous cells.

In some instances, the compositions comprising one or more generally regarded as safe (GRAS) compounds selected from the group of components consisting of vitamins, selenium, fatty acids, fatty acid salts, and fatty acid esters, or their pharmaceutically acceptable salts, are used in combination with various anticancer drugs give rise to a significantly enhanced cytotoxic or anti-neoplastic effect on cancerous cells, and thus provide an increased therapeutic effect. Specifically, a significantly increased kill rate is obtained with the above-disclosed combinations with the anticancer drugs compared to the treatment regimes in which the drugs are used alone. Such combinations provide therapy wherein a greater anti-neoplastic effect than can be achieved from the anticancer drugs used in standard treatment regimes, enhancing the effectiveness of the therapy, decreasing the amount of anticancer compounds needed to achieve an effective dose, and/or reducing the total number of treatments required.

The foregoing aspects are realized in one aspect by providing a combination comprising a first and second agent. The first agent comprises a composition comprising one or more generally regarded as safe (GRAS) compounds selected from the group of components consisting of vitamins, selenium, fatty acids, fatty acid salts, and fatty acid esters, or their pharmaceutically acceptable salts, and the second agent comprises cisplatin, cisplatin-based therapies, carboplatin, mitomycin, vincristine, methotrexate, fluorouracil, calcium folinate, cytosine arabinoside, cyclophosphamide, epirubicin, etoposide, bleomycin A5, taxanes, mitoxanthrone, cylcophosphamide, topoisomerase inhibitors, angiogenesis inhibitors, cisplatin-based therapies, differentiation agents, signal transduction inhibitors, busulfan, doxorubicin rapid dissolution, etoposide, 5-fluorouracil, tamoxifen, or combinations thereof. The first and second agents are suitably present in therapeutically effective amounts and work synergistically to kill and/or inhibit the growth of human cancer cells.

Also provided are methods of synergistically killing human cancer cells. The methods comprise contacting the cells with a composition comprising one or more generally regarded as safe (GRAS) compounds selected from the group of components consisting of vitamins, selenium, fatty acids, fatty acid salts, and fatty acid esters, or their pharmaceutically acceptable salts, an optional pH modulator such as $Na_2CO_3$, and a second composition which comprises an agent selected from the group consisting of cisplatin, cisplatin-based therapies, carboplatin, mitomycin, vincristine, methotrexate, fluorouracil, calcium folinate, cytosine arabinoside, cyclophosphamide, epirubicin, etoposide, bleomycin A5, taxanes, mitoxanthrone, cylcophosphamide, topoisomerase inhibitors, angiogenesis inhibitors, cisplatin-based therapies, differentiation agents, signal transduction inhibitors, busulfan, doxorubicin rapid dissolution, etoposide, 5-fluorouracil, tamoxifen, or combinations thereof.

Also provided are compositions comprising a therapeutic combination of one or more agents selected from a composition comprising one or more generally regarded as safe (GRAS) compounds selected from the group of components consisting of vitamins, selenium, fatty acids, fatty acid salts, and fatty acid esters, or their pharmaceutically acceptable salts.

Also provided are combinations of a composition comprising one or more generally regarded as safe (GRAS) compounds selected from the group of components consisting of vitamins, selenium, fatty acids, fatty acid salts, and fatty acid esters, or their pharmaceutically acceptable salts, and anticancer agents that work additively. In this aspect of the invention, a therapeutic combination is provided. The therapeutic combination comprises a first agent which is selected from a composition comprising one or more generally regarded as safe (GRAS) compounds selected from the group of components consisting of vitamins, selenium, fatty acids, fatty acid salts, and fatty acid esters, or their pharmaceutically acceptable salts, and a second agent which is selected from the group consisting of cisplatin, cisplatin-based therapies, carboplatin, mitomycin, vincristine, methotrexate, fluorouracil, calcium folinate, cytosine arabinoside, cyclophosphamide, epirubicin, etoposide, bleomycin A5, taxanes, mitoxanthrone, cylcophosphamide, topoisomerase inhibitors, angiogenesis inhibitors, cisplatin-based therapies, differentiation agents, signal transduction inhibitors, busulfan, doxorubicin rapid dissolution, etoposide, 5-fluorouracil, tamoxifen, or combinations thereof. The first and second agents have additive properties for killing human cancer cells.

Also provided are combinations for the inhibition of growth of human cancer cells. The combination comprises a therapeutically effective dose of an additive combination of a first agent which is selected from a composition comprising one or more generally regarded as safe (GRAS) compounds selected from the group of components consisting of vitamins, selenium, fatty acids, fatty acid salts, and fatty acid esters, or their pharmaceutically acceptable salts, and a second agent which is selected from the group consisting of cisplatin, cisplatin-based therapies, carboplatin, mitomycin, vincristine, methotrexate, fluorouracil, calcium folinate, cytosine arabinoside, cyclophosphamide, epirubicin, etoposide, bleomycin A5, taxanes, mitoxanthrone, cylcophosphamide, topoisomerase inhibitors, angiogenesis inhibitors, cisplatin-based therapies, differentiation agents, signal transduction inhibitors, busulfan, doxorubicin rapid dissolution, etoposide, 5-fluorouracil, tamoxifen, or combinations thereof.

In another embodiment the invention provides a method of additively inhibiting the growth of cancer cells. The method comprises contacting cancer cells with a first composition which comprises a compound or compounds selected from a composition comprising one or more generally regarded as safe (GRAS) compounds selected from the group of components consisting of vitamins, selenium, fatty acids, fatty acid salts, and fatty acid esters, or their pharmaceutically acceptable salts and a second composition which comprises an agent selected from the group consisting of cisplatin, cisplatin-based therapies, carboplatin, mitomycin, vincristine, methotrexate, fluorouracil, calcium folinate, cytosine arabinoside, cyclophosphamide, epirubicin, etoposide, bleomycin A5, taxanes, mitoxanthrone, cylcophosphamide, topoisomerase inhibitors, angiogenesis inhibitors, cisplatin-based therapies, differentiation agents, signal transduction inhibitors, busulfan, doxorubicin rapid dissolution, etoposide, 5-fluorouracil, tamoxifen, or combinations thereof.

Effective amounts of an active composition comprising one or more generally regarded as safe (GRAS) compounds selected from the group of components consisting of vitamins, selenium, fatty acids, fatty acid salts, and fatty acid esters, or their pharmaceutically acceptable salts compounds can be administered to patients with cancer or neoplasms. When administered the abnormal neoplastic cells are killed and/or the proliferative activity of the abnormal neoplastic cells is inhibited, reduced, or stabilized.

The effective amounts of a composition comprising one or more generally regarded as safe (GRAS) compounds selected from the group of components consisting of vitamins, selenium, fatty acids, fatty acid salts, and fatty acid esters, or their pharmaceutically acceptable salts, and chemotherapeutic agents can be given in an administration protocol in a variety of administration protocols and dose ranges depending on the particular need of the patient.

Administration of a composition comprising one or more generally regarded as safe (GRAS) compounds selected from the group of components consisting of vitamins, selenium, fatty acids, fatty acid salts, and fatty acid esters, or their pharmaceutically acceptable salts, may as a stand-alone treatment or be administered prior to, simultaneous with, or after administration of other therapeutic agents.

All routes of administration of the composition comprising one or more generally regarded as safe (GRAS) compounds selected from the group of components consisting of vitamins, selenium, fatty acids, fatty acid salts, and fatty acid esters, or their pharmaceutically acceptable salts, or its co-administration with other therapeutic agents are suitable. However, co-administration of a composition comprising one or more generally regarded as safe (GRAS) compounds selected from the group of components consisting of vitamins, selenium, fatty acids, fatty acid salts, and fatty acid esters, or their pharmaceutically acceptable salts, alone, or in combination with other agents, during systemic administration and peritoneal treatment programs such as HIPEC or IP provides advantages over other treatment modalities.

Also provided are pharmaceutical compositions containing the one or more GRAS compounds (e.g., as described above) and optionally one or more additional chemotherapeutic agents, e.g., as may be employed in the subject methods. Accordingly, the one or more GRAS compounds can be formulated for oral or parenteral administration for use in the subject methods, e.g., in the form of a pharmaceutically acceptable salt, as described above. In certain embodiments, e.g., where the compounds are administered as separate formulations (such as in those embodiments where they are administered sequentially), separate or distinct pharmaceutical compositions, each containing a different active agent, are provided. In yet other embodiments, a single formulation that includes both of one or more GRAS compounds and one or more chemotherapeutic agents (i.e., one composition that includes both active agents) is provided.

By way of illustration, the active agent(s) can be admixed with conventional pharmaceutically acceptable carriers and excipients (i.e., vehicles) and used in the form of aqueous solutions, tablets, capsules, elixirs, suspensions, syrups, wafers, and the like. Such pharmaceutical compositions contain, in certain embodiments, from about 0.1 to about 90% by weight of the active compound, and more generally from about 1 to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example, a powder containing active compound, suspending agent, sucrose and a sweetener can be reconstituted with water to form a suspension, and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil; for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration.

A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetracetic acid, and an anti-oxidant, for example, sodium metabisulphite may be included in the formulation. Alternatively, the solution can be freeze dried and then reconstituted with a suitable solvent just prior to administration.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, herein incorporated by reference in its entirety). Such patches may be constructed for continuous, pulsatile, or on demand delivery of pharmaceutical agents.

In certain embodiments of interest, one or more GRAS compounds (e.g., as described above) and one or more chemotherapeutic agents are administered as a single pharmaceutical formulation, that may include other suitable compounds and carriers, and also may be used in combination with other active agents. The present invention, therefore, also includes pharmaceutical compositions comprising pharmaceutically acceptable excipients. The pharmaceutically acceptable excipients include, for example, any suitable vehicles, adjuvants, carriers or diluents, and are readily available to the public. The pharmaceutical compositions of the present invention may further contain other active agents as are well known in the art.

One skilled in the art will appreciate that a variety of suitable methods of administering a formulation of the present invention to a subject or host, e.g., patient, in need thereof, are available, and, although more than one route can be used to administer a particular formulation, a particular route can provide a more immediate and more effective reaction than another route. Pharmaceutically acceptable excipients are also well-known to those who are skilled in the art, and are readily available. The choice of excipient will be determined in part by the particular compound, as well as by the particular method used to administer the composition. Accordingly, there are a wide variety of suitable formulations of the pharmaceutical composition of the present invention. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art to be appropriate.

The subject formulations of the present invention can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are known in the art to be appropriate.

Suppository formulations are also provided by mixing with a variety of bases such as emulsifying bases or watersoluble bases. Formulations suitable for vaginal administration may be presented as pessaries, tampons, creams, gels, pastes, foams.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Those of skill in the art will readily appreciate that dose levels can vary as a function of the specific compound, the nature of the delivery vehicle, and the like. Suitable dosages for a given compound are readily determinable by those of skill in the art by a variety of means.

The dose administered to an animal, particularly a human, in the context of the present invention should be sufficient to elicit a prophylactic or therapeutic response in the animal over a reasonable time frame. One skilled in the art will recognize that dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound. Suitable doses and dosage regimens can be determined by comparisons to anticancer or immunosuppressive agents that are known to elicit the desired growth inhibitory or immunosuppressive response. In the treatment of some individuals with the compounds of the present invention, it may be desirable to use a high dose regimen in conjunction with a rescue agent for non-malignant cells. In such treatment, any agent capable of rescue of non-malignant cells can be employed, such as citrovorum factor, folate derivatives, or leucovorin. Such rescue agents are well known to those of ordinary skill in the art. Rescue agents include those which do not interfere with the ability of the present inventive compounds to modulate cellular function.

In another embodiment, the aqueous cyclodextrin solution further comprises dextrose, e.g., about 5% dextrose. Other components suitable for use in the formulations of the present invention can be found in Remington's Pharmaceutical Sciences, Mace Publishing Company, Philadelphia, Pa., 17th ed. (1985).

An expanded appreciation of specific adaptations, compositional variations, and physical attributes will be gained upon an examination of the following detailed description of preferred embodiments, taken in conjunction with the appended claims.

EXPERIMENTAL

Methods
General:

For each study, two plates of HCT-116 cells were seeded in 96-well cell culture plates (2000 cells per well for three-day studies and 10,000 cells for one-day studies). The next day, drugs prepared in 200 µl of culture medium were added to the wells. Control wells had culture medium containing the same amount of solvents used to dissolve the drugs. Each treatment was completed in triplicate. One plate was incubated at 37° C. while the other plate was incubated at 42° C. (hyperthermia) for one hour (two hours for study 7 and 8). After the treatment, 4000 freshly harvested cells (cells which were not subjected to hyperthermia) were added to 3 wells of each plate to assess the effect of hyperthermia (for one-day experiments, 20,000 cells will be added). Both plates were incubated at 37° C. for the number of days specified in each study. Cell viability was measured using MTS assay (Promega CellTiter 96 Aqueous MTS Assay reagents).

Study 1:

Established cell killing curves of Mitomycin C and Cisplatin on HCT-116 cells. Mitomycin C (120 µM, 80 µM, 8 µM, 0.8 µM, 0.08 µM and 0.008 µM) and Cisplatin (100 µM, 50 µM, 5 µM, 0.5 µM, 0.05 µM and 0.005 µM) were tested. Cytotoxicity was measured after three days.

Study 2:

Established cell killing curves of five non-chemo reagents on HCT-116 cells. Vitamin C (20 mM, 5 mM, 1.25 mM, 0.3125 mM and 0.078 mM), Vitamin D (200 nM, 40 nM, 8 nM, 1.6 nM and 0.32 nM), Vitamin E (200 µM, 40 µM, 8 µM, 1.6 µM and 0.32 µM), Selenite (500 µM, 100 µM, 20 µM, 4 µM and 0.8 µM) and Quercetin (300 µM, 100 µM, 33.3 µM, 11.1 µM and 3.7 µM) were tested. Cytotoxicity was measured after three days.

Study 3:

Tested the cytotoxic effects of combination treatments (±hyperthermia at 42° C. for one hour) with chemotherapeutic reagents (Mitomycin C at 0.2 and 0.8 µM or Cisplatin at 2.5 and 10 µM) and three non-chemotherapeutic reagents (1.25 mM Vitamin C, 20 µM Selenite and 150 µM Quercetin). The non-chemotherapeutic agent combinations tested were: Vitamin C/Selenite and Vitamin C/Selenite/Quercetin. Cytotoxicity was measured after three days.

Study 4:

Tested the cytotoxic effects of combination treatments (±hyperthermia at 42° C. for one hour) with chemotherapeutic reagents (Mitomycin C at 0.2 and 0.8 µM or Cisplatin at 2.5 and 10 µM) and three non-chemotherapeutic reagents (40 µM Vitamin E, 20 µM Selenite and 150 µM Quercetin). The non-chemotherapeutic agent combinations tested were: Vitamin E/Selenite/Quercetin and Selenite/Quercetin. Cytotoxicity was measured after three days.

Study 5:

Tested the cytotoxic effects of combination treatments (±hyperthermia at 42° C. for one hour) with chemotherapeutic reagents (Mitomycin C at 0.2 and 0.8 µM or Cisplatin at 2.5 and 10 µM) and four non-chemotherapeutic reagents (100 nM Vitamin D, 40 µM Vitamin E, 20 µM Selenite and 150 µNA Quercetin). The non-chemotherapeutic agent combinations tested were: Quercetin/Vitamin D/Vitamin E/Selenite, Vitamin E/Selenite, and Vitamin D/Vitamin E/Selenite. Cytotoxicity was measured after three days.

Study 6:

Tested the cytotoxic effects of combination treatments (±hyperthermia at 42° C. for one hour) with chemotherapeutic reagents (0.2 μM Mitomycin C or 10 μM Cisplatin) and three non-chemotherapeutic reagents (1.25 mM Vitamin C, 20 μM Selenite and 150 μM Quercetin and also combinations with half concentrations). The non-chemotherapeutic agent combinations tested were: Vitamin C/Selenite, Vitamin C/Quercetin, Selenite/Quercetin and Vitamin C/Selenite/Quercetin. Cytotoxicity was measured after three days.

Study 7:

Tested the short-term cytotoxic effects of combination treatments (±hyperthermia at 42° C. for two hour) with chemotherapeutic reagents (0.2 μM Mitomycin C or 10 μM Cisplatin) and three non-chemotherapeutic reagents (1.25 mM Vitamin C, 20 μM Selenite and 150 μM Quercetin). The non-chemotherapeutic agent combinations tested were: Vitamin C/Quercetin and Vitamin C/Selenite/Quercetin. Three conditions were tested in the study:

a. Cytotoxicity was measured with MTS assay immediately after the two-hour drug/hyperthermia treatment.
b. Cells were treated with drugs for two hours. Drugs were replaced with fresh medium after the treatment, and the cytotoxic effect was measured after one day.
c. Cells were incubated with drugs for one day before the cytotoxicity was measured.

Study 8:

Tested the cytotoxic effects of two-hour combination treatments (±hyperthermia at 42° C. for two hour) with chemotherapeutic reagents (0.2 μM Mitomycin C or 10 μM Cisplatin) and three non-chemotherapeutic reagents (1.25 mM Vitamin C, 20 μM Selenite and 150 μM Quercetin). The non-chemotherapeutic agent combinations tested were: Vitamin C/Quercetin and Vitamin C/Selenite/Quercetin. Drugs were replaced with fresh medium after the treatment, and cytotoxic effect were measured after three days.

Results

Figure 1B:
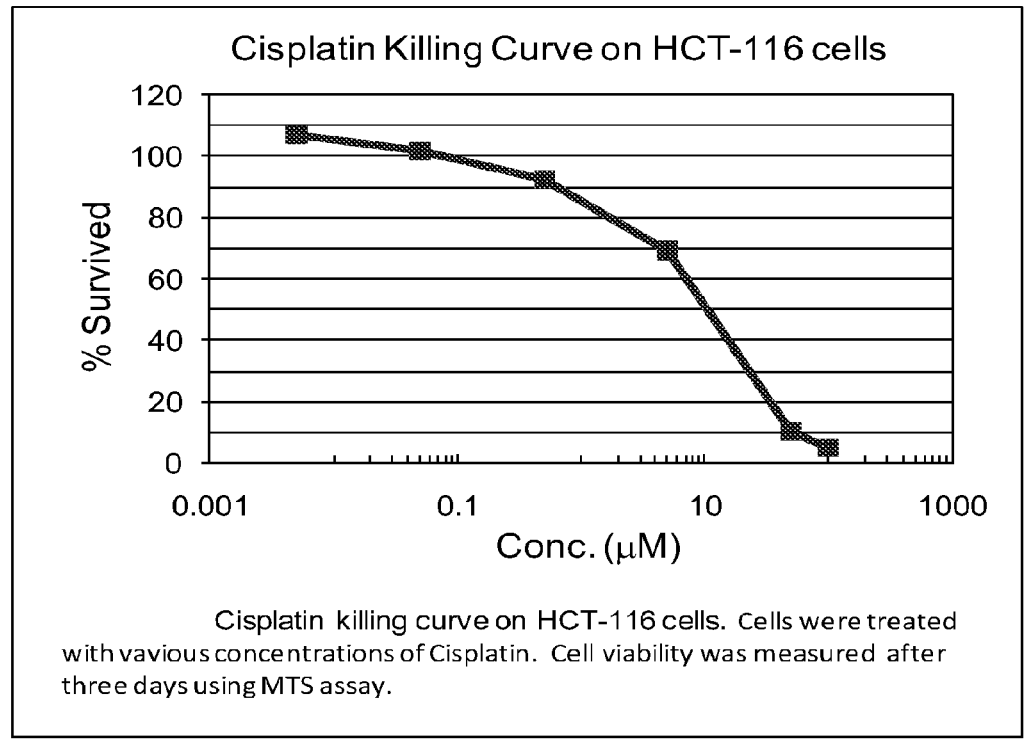

Study 1:

The assay conditions and cell killing curves for two chemotherapeutic reagents, Mitomycin C and Cisplatin, were established (FIGS. 1a and 1b). Growth inhibition ($GI_{50}$) of Mitomycin C was 1.3 μM (FIG. 1a) and the $GI_{50}$ of Cisplatin was 12 μM (FIG. 1b) for HCT-116 cells.

Study 2: The cell killing curves for five non-chemotherapeutic reagents (Vitamin C, Vitamin D, Vitamin E, Selenite and Quercetin) were established for HCT-116 cells (FIG. 2a-e).

FIG. 2a:
i) $GI_{50}$ of vitamin C on HCT-116 cells was approximately 2 mM.
ii) Hyperthermia treatment had a significant effect on cells treated with 0.08 mM (% cell survival of 37° C. vs 42° C. 1 hr: 102% vs 92.6%, with a significance level P=0.03, one-tailed paired T-test) and 0.31 mM (% cell survival of 37° C. vs 42° C. 1 hr treatment: 97.6% vs 89% at a significance level of P=0.02, one-tailed paired T-test).

FIG. 2b:
i) Vitamin D did not show significant growth inhibition on HCT116 cells at the concentrations tested. In fact, there was a slight growth promoting effect at the higher concentrations tested.
ii) Hyperthermia treatment had significant effect on cells treated with 200 nM (cell survival of 37° C. vs 42° C. 1 hr: 122% vs 110%, with a significance level of P=0.05, one-tailed paired T-test).

FIG. 2c:
i) $GI_{50}$ of Vitamin E on HCT-116 cells was approximately 90 μM. There was a slight growth promoting effect at the lower concentrations tested for 37° C. treated group.
ii) Hyperthermia treatment had a significant effect the growth of cells treated with 0.32 μM of Vitamin E (% cell survival of 37° C. vs 42° C. 1 hr treatment: 111% vs 95.5%, with a significance level of P=0.003, one-tailed paired T-test) and 1.6 μM (% cell survival of 37° C. vs 42° C. 1 hr treatment: 116% vs 102% at a significance level of P=0.01, one-tailed paired T-test).

FIG. 2d:
i) $GI_{50}$ of Selenite on HCT-116 cells was approximately 30 μM.
ii) No significant effect on cell growth was observed by hyperthermia treatment.

Figure 2E:
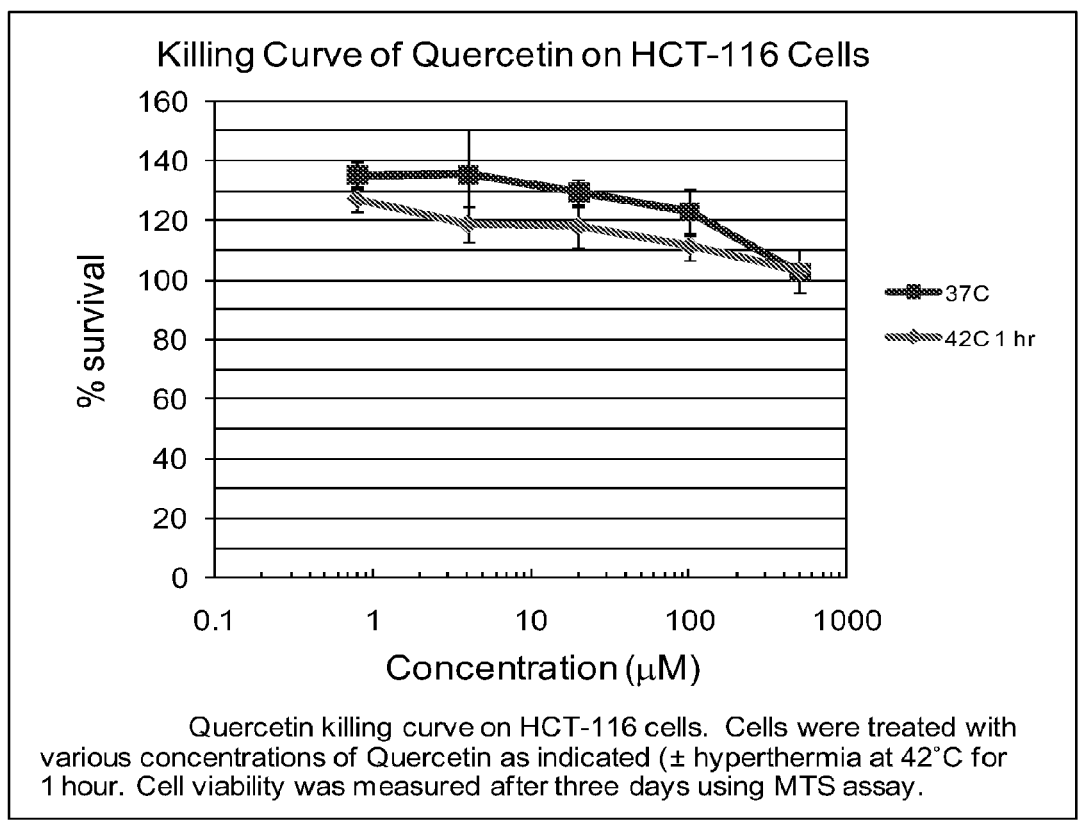

FIG. 2e:
i) Quercetin did not show significant growth inhibition on HCT116 cells at the concentrations tested. There was a slight growth promoting effect at the lower concentrations tested.
ii) Hyperthermia treatment had a significant effect on cells treated with 20 μM (% cell survival of 37° C. vs 42° C. 1 hr treatment: 129% vs 118%, with a significance level of P=0.02, one-tailed paired T-test) and 100 μM (% cell survival of 37° C. vs 42° C. 1 hr treatment: 123% vs 111% at a significance level of P=0.04, one-tailed paired T-test).

Study 3:

Tested combinations of chemotherapeutic agents (Mitomycin C and Cisplatin at two different concentrations) and three non-chemotherapeutic agents (Vitamin C, Selenite and Quercetin) with the human colon cancer cell line HCT-116 using MTS assays. We observed a synergic effect in cancer cell killing with certain combination of agents. We found that hyperthermia enhanced the growth inhibition effect exerted by certain combinations of test compound treatments.

Figure 3A:
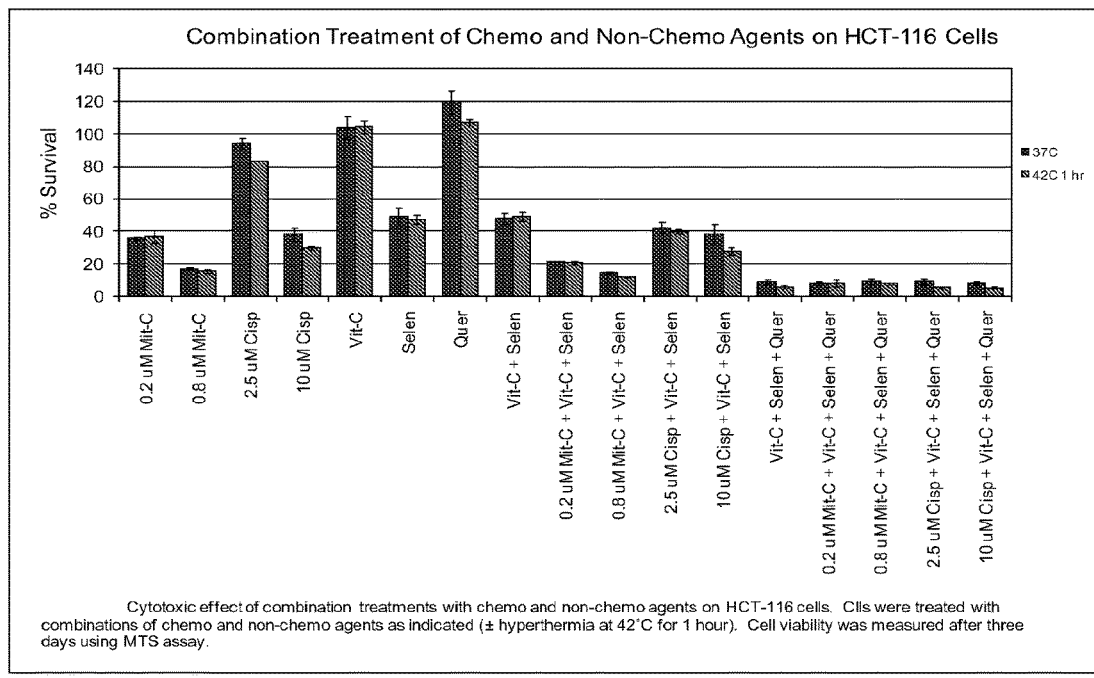

FIG. 3a: Hyperthermia Treatment had an Effect on:
i) 150 μM Quercetin treatment (% cell survival of 37° C. vs 42° C. 1 hr treatment: 128% vs 107%, with a significance level of P=0.02, one-tailed paired T-test).
ii) 0.8 μM Mitomycin C/Vit-C/Selenite treatment (% cell survival of 37° C. vs 42° C. 1 hr treatment: 14.8% vs 12.1% at a significance level of P=0.03, one-tailed paired T-test).
iii) 2.5 μM Cisplatin treatment (% cell survival of 37° C. vs 42° C. 1 hr treatment: 95.2% vs 82.7%, with a significance level of P=0.02, one-tailed paired T-test) and 10 μM Cisplatin treatment (% cell survival of 37° C. vs 42° C. 1 hr treatment: 41.2% vs 29.9% at a significance level of P=0.02, one-tailed paired T-test).
iv) 10 μM Cisplatin/Vit-C/Selenite treatment (% cell survival of 37° C. vs 42° C. 1 hr treatment: 38.2% vs 27.6% at a significance level of P=0.02, one-tailed paired T-test).
v) Vit-C/Selenite/Quercetin treatment (% cell survival of 37° C. vs 42° C. 1 hr treatment: 8.7% vs 6.0% at a significance level of P=0.01, one-tailed paired T-test); 2.5 μM Cisplatin/Vit-C/Selenite/Quercetin treatment (% cell survival of 37° C. vs 42° C. 1 hr treatment: 9.4% vs 5.5% at a significance level of P=0.02, one-tailed paired T-test) and 10 μM Cisplatin/Vit-C/Selenite/Quercetin treatment (% cell survival of 37° C. vs 42° C. 1 hr treatment: 8.3% vs 5.3% at a significance level of P=0.003, one-tailed paired T-test).

FIG. 3a shows that the combination of Vit-C and Selenite resulted in synergistic gains in effectiveness for both of the chemotherapeutic agents, mitomycin and cisplatin. FIG. 3a also shows that the combination of Vit-C, Selenite, and Quercetin resulted in dramatic killing of cancer cells with synergistic gains in effectiveness for both of the chemotherapeutic agents, mitomycin and cisplatin.

Figure 3B:
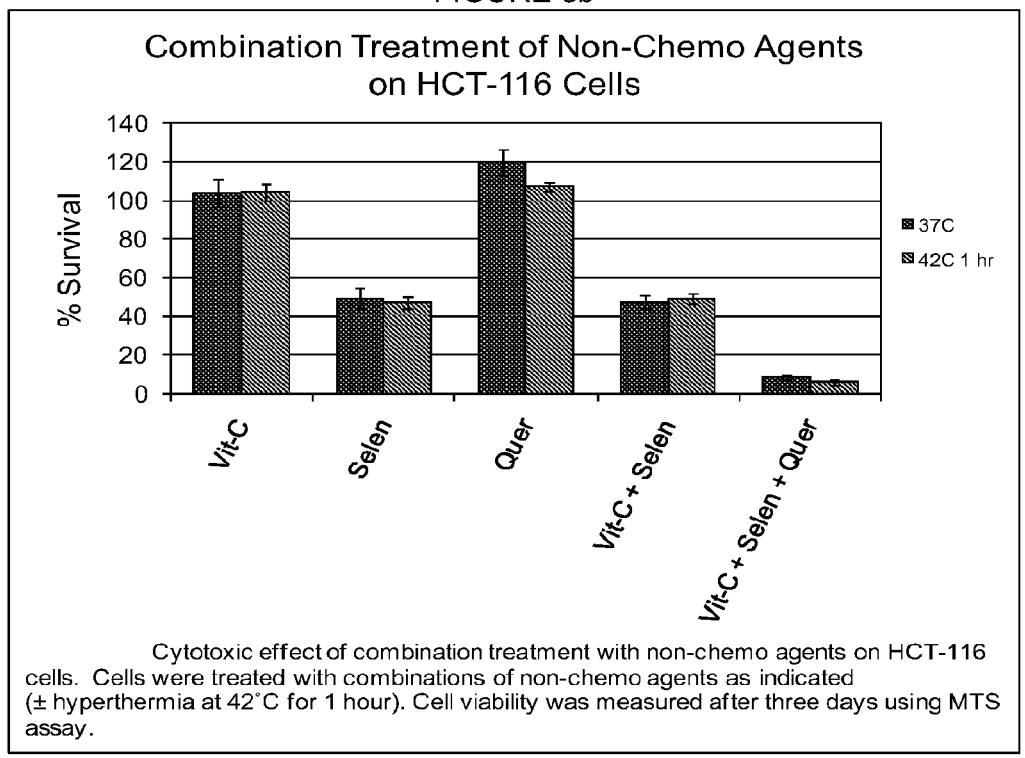

FIG. 3b: Even though Quercetin treatment alone (150 µM) did not show enhanced killing of HCT-116 cells, it did enhance cell killing when combined with Vitamin C/Selenite (% cell survival at 37° C.: Vit-C/selenite 47.7% vs Vit-C/selenite/Quercetin 8.7%; % cell survival at 42° C.: Vit-C/selenite 49.1% vs Vit-c/selenite/Quercetin 6.0%).

FIG. 3b shows that the combination of Vit-C and Selenite resulted in synergistic gains in cancer cell killing when compared to either agent alone. FIG. 3b also shows that the combination of Vit-C, Selenite, and Quercetin resulted in dramatic synergy of cancer cells killing ability when compared to the agents on their own.

Figure 3C:
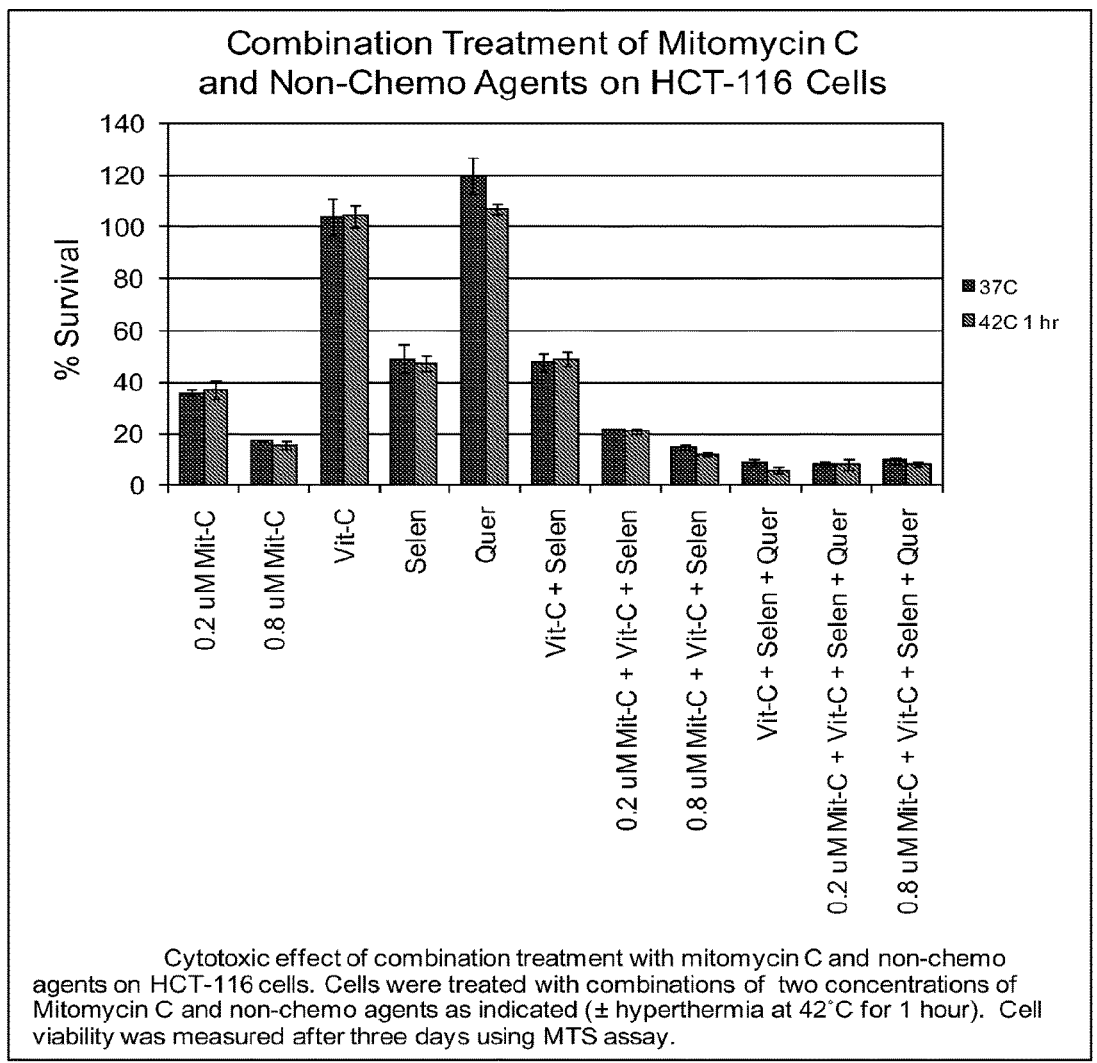

FIG. 3c:
i) Combination of Mitomycin C with Vitamin C/Selenite enhanced the killing of HCT-116 cells when compared with either treatment alone.
ii) % cell survival at 37° C.: 0.2 µM Mit-C/Vit-C/selenite 21.4%, 0.2 µM Mit-C 35% and Vit-C/selenite 47.7%.
iii) % cell survival at 42° C.: 0.2 µM Mit-C/Vit-C/selenite 21.1%, 0.2 µM Mit-C 36.9% and Vit-C/selenite 49.1%.
iv) % cell survival at 37° C.: 0.8 µM Mit-C/Vit-C/selenite 14.8%, 0.8 µM Mit-C 16.9% and Vit-C/selenite 47.7%.
v) % cell survival at 42° C.: 0.8 µM Mit-C/Vit-C/selenite 12.1%, 0.8 µM Mit-C 15.5% and Vit-C/selenite 49.1%.

FIG. 3c shows that the combination of Vit-C and Selenite resulted in synergistic gains in effectiveness for the chemotherapeutic agent mitomycin. FIG. 3c also shows that the combination of Vit-C, Selenite, and Quercetin resulted in dramatic killing of cancer cells with synergistic gains in effectiveness for the chemotherapeutic agent mitomycin.

Figure 3D:
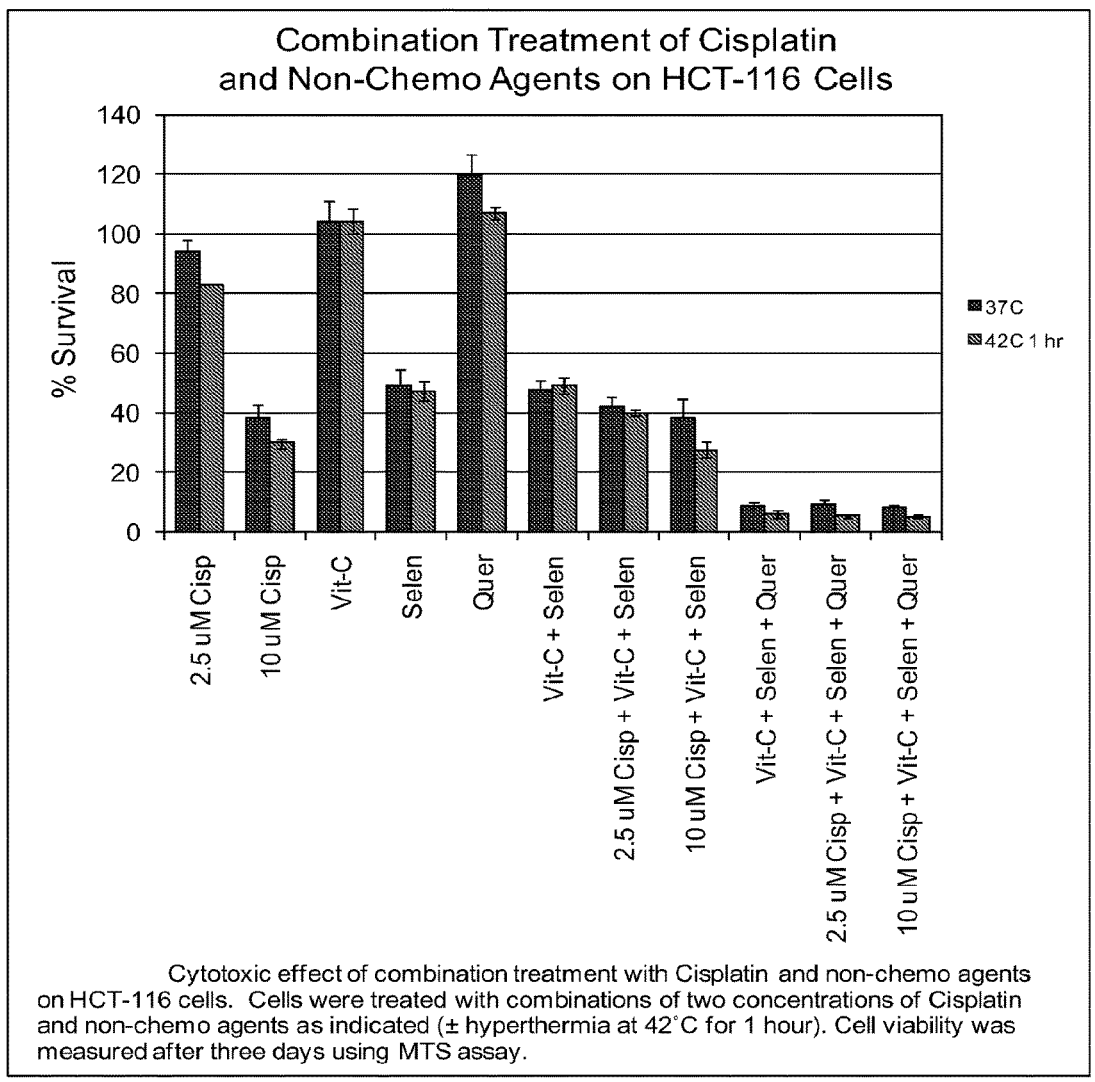

FIG. 3d:
i) Cisplatin enhanced the killing of HCT-116 cells when combined with Vitamin C/Selenite.
ii) % cell survival at 37° C.: 2.5 µM Cisp/Vit-C/selenite 42.1% vs Vit-C/selenite 47.7% (P=0.03, one-tailed T-test).
iii) % cell survival at 42° C.: 2.5 µM Cisp/Vit-C/selenite 39.9% vs Vit-C/selenite 49.1% (P=0.001, one-tailed).
iv) % cell survival at 37° C.: 10 µM Cisp/Vit-C/selenite 38.2% vs Vit-C/selenite 47.7% (P=0.01, one-tailed).
v) % cell survival at 42° C.: 10 µM Cisp/Vit-C/selenite 27.6% vs Vit-C/selenite 49.1% (P=0.0001, one-tailed).

FIG. 3d shows that the combination of Vit-C and Selenite resulted in synergistic gains in effectiveness for the chemotherapeutic agent cisplatin. FIG. 3d also shows that the combination of Vit-C, Selenite, and Quercetin resulted in dramatic killing of cancer cells with synergistic gains in effectiveness for the chemotherapeutic agent cisplatin.

Study 4:
Tested combinations of chemotherapeutic agents (Mitomycin C and Cisplatin at two different concentrations) and three non-chemotherapeutic agents (Vitamin E, Selenite and Quercetin) with the human colon cancer cell line HCT-116 using MTS assays. We observed a synergic effect in cancer cell killing with certain combination of agents. We also found that hyperthermia enhanced the growth inhibition effect of certain combination of test compound treatments.

Figure 4A:
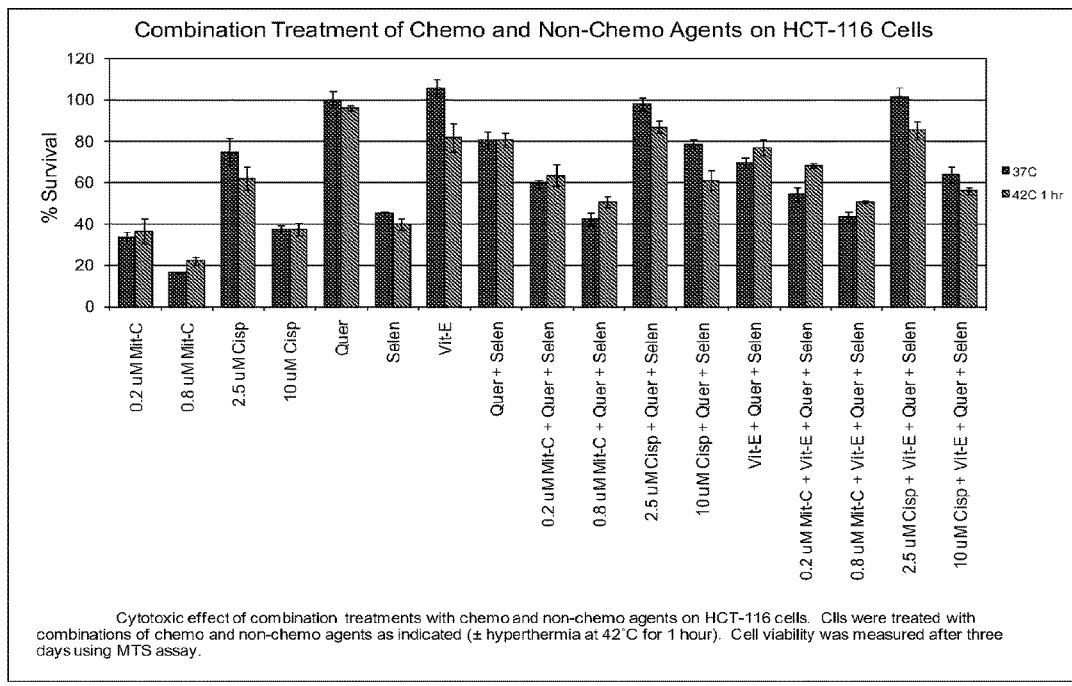

FIG. 4a: Hyperthermia Treatment had an Effect on:
i) Control cells without treatment (solvent only control) (% cell survival of 37° C. vs 42° C. 1 hr treatment: 103.2% vs 91.9% at a significance level of P=0.003, one-tailed paired T-test).
ii) 0.8 µM Mitomycin C treatment (% cell survival of 37° C. vs 42° C. 1 hr treatment: 16.4% vs 22.1% at a significance level of P=0.02, two-tailed paired T-test).
iii) 2.5 µM Cisplatin treatment (% cell survival of 37° C. vs 42° C. 1 hr treatment: 74.7% vs 61.7% at a significance level of P=0.01, one-tailed paired T-test).
iv) 20 µM Selenite treatment (% cell survival of 37° C. vs 42° C. 1 hr treatment: 45.0% vs 39.7% at a significance level of P=0.03, one-tailed paired T-test).
v) 40 µM Vitamin E treatment (% cell survival of 37° C. vs 42° C. 1 hr treatment: 105.7% vs 81.6% at a significance level of P=0, one-tailed paired T-test).
vi) 2.5 µM Cisplatin/Quercetin/Selenite treatment (% cell survival of 37° C. vs 42° C. 1 hr treatment: 97.8% vs 86.7% at a significance level of P=0.001, one-tailed paired T-test); 10 µM Cisplatin/Quercetin/Selenite treatment (% cell survival of 37° C. vs 42° C. 1 hr treatment: 78.6% vs 61.0% at a significance level of P=0.01, one-tailed paired T-test).
vii) 0.2 µM Mitomycin C/Vit-E/Quercetin/Selenite treatment (% cell survival of 37° C. vs 42° C. 1 hr treatment: 54.3% vs 68.20% at a significance level of P=0.04, two-tailed paired T-test); 0.8 µM Mitomycin C/Vit-E/Quercetin/Selenite treatment (% cell survival of 37° C. vs 42° C. 1 hr treatment: 43.2% vs 50.6% at a significance level of P=0.03, two-tailed paired T-test).
viii) 2.5 µM Cisplatin/Vit-E/Quercetin/Selenite treatment (% cell survival of 37° C. vs 42° C. 1 hr treatment: 101.4% vs 85.1% at a significance level of P=0.001, one-tailed paired T-test); 10 µM Cisplatin/Vit-E/Quercetin/Selenite treatment (% cell survival of 37° C. vs 42° C. 1 hr treatment: 63.8% vs 56.1% at a significance level of P=0.01, one-tailed paired T-test).

FIG. 4a shows that the combination of Quercitin and Selenite did not result in synergistic gains in effectiveness for either of the chemotherapeutic agents, mitomycin and cisplatin. FIG. 4a also shows that the combination of Vit-E, Selenite, and Quercetin did not result in synergistic gains in effectiveness for either of the chemotherapeutic agents, mitomycin and cisplatin.

Figure 4B:
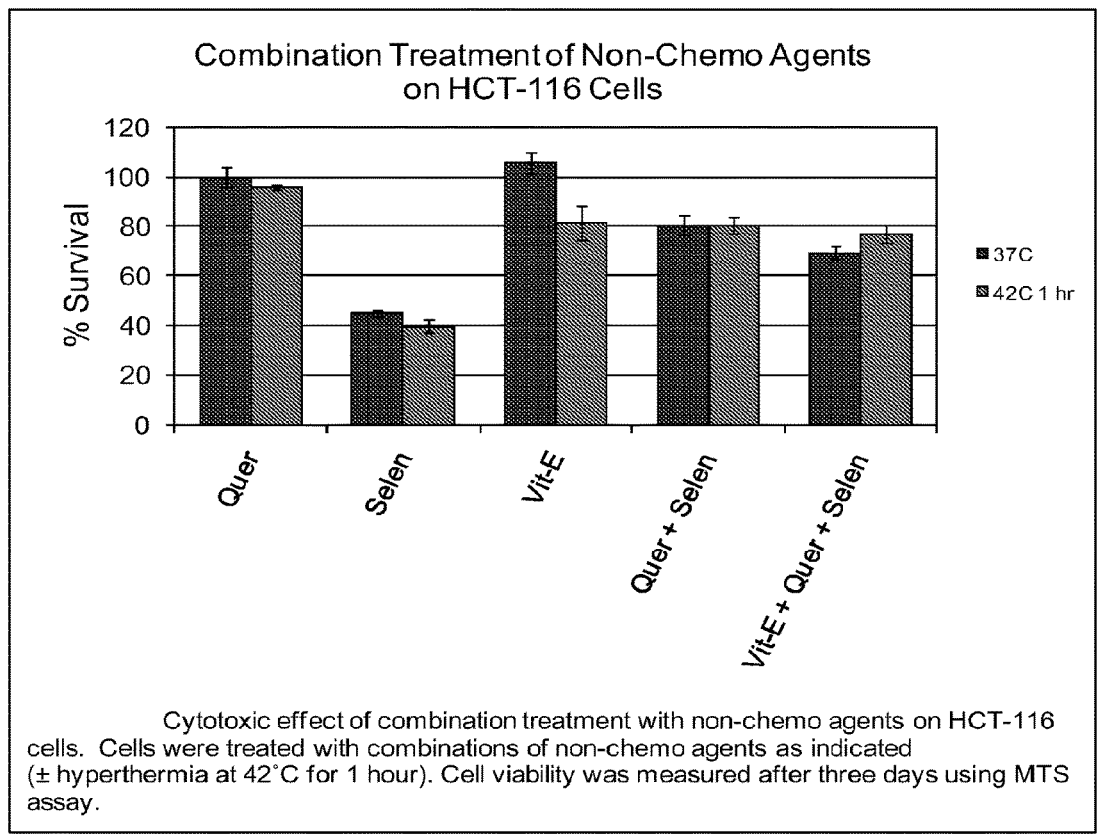

FIG. 4b:
i) Quercetin reduced the cytotoxicity of Selenite.
ii) % cell survival at 37° C.: Selenite 45%; Quercetin/Selenite 80.5%. % cell survival at 42° C.: Selenite 39.8%; Quercetin/Selenite 80.5%.
iii) Vitamin E did not appear to have additional effects on Quercetin/Selenite treatment.

Figure 4C:
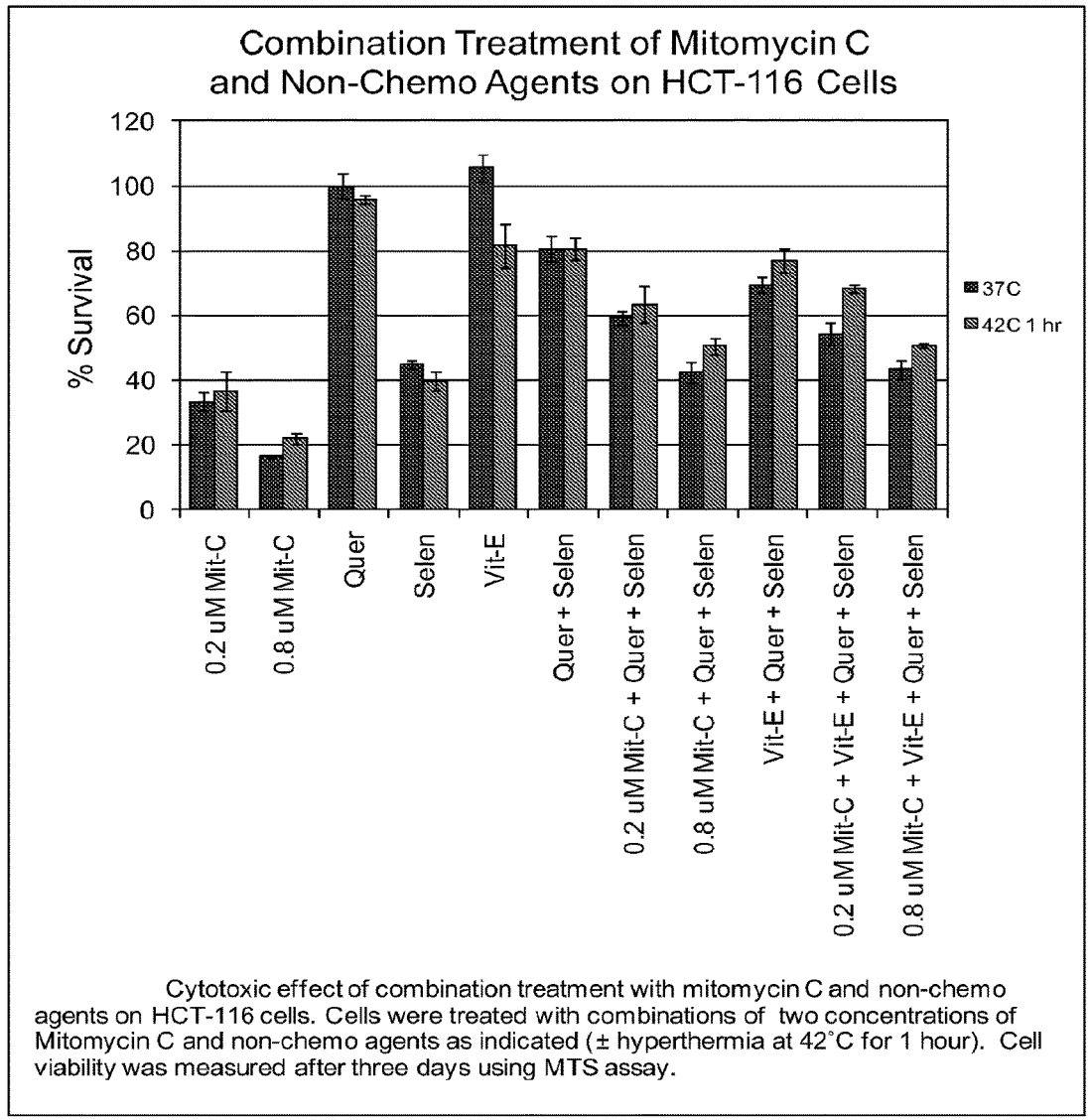

FIG. 4c:
i) Addition of Quercetin/Selenite reduced the cytotoxicity of Mitomycin C on HCT-116 cells.
ii) % cell survival at 37° C.: 0.2 µM Mit-C/Quercetin/Selenite 59.2%, 0.2 µM Mit-C 33.3%.
iii) % cell survival at 42° C.: 0.2 µM Mit-C/Quercetin/Selenite 63.4%, 0.2 µM Mit-C 36.5%.
iv) % cell survival at 37° C.: 0.8 µM Mit-C/Quercetin/Selenite 42.2%, 0.8 µM Mit-C 16.4%.
v) % cell survival at 42° C.: 0.8 µM Mit-C/Quercetin/Selenite 50.5%, 0.8 µM Mit-C 22.1%.
vi) Vitamin E did not seem to have additional effects on Mit-C/Quercetin/Selenite treatment.

FIG. 4c shows that the combination of Quercetin and Selenite did not result in synergistic gains in effectiveness for the chemotherapeutic agent mitomycin. FIG. 4c also shows that the combination of Vit-E, Selenite, and Quercetin did not result in synergistic gains in effectiveness for the chemotherapeutic agent mitomycin.

Figure 4D:
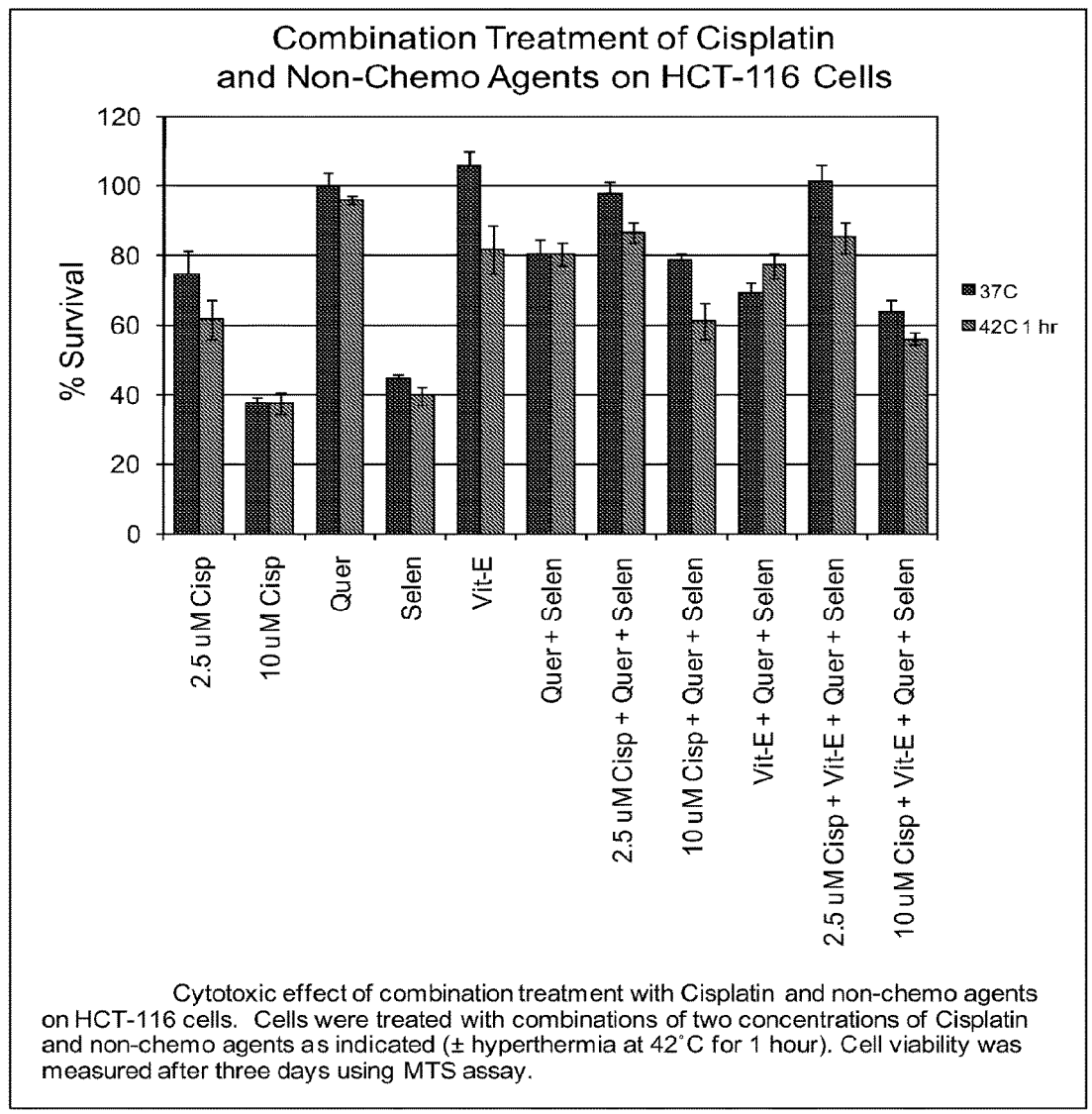

FIG. 4d:
- i) The combination of Quercetin/Selenite with Cisplatin reduced the cytotoxicity of Cisplatin on HCT-116 cells.
- ii) % cell survival at 37° C.: 2.5 µM Cisp/Quercetin/Selenite 97.8%, 2.5 µM Cisp 74.7%.
- iii) % cell survival at 42° C.: 2.5 µM Cisp/Quercetin/Selenite 86.7%, 2.5 µM Cisp 61.7%.
- iv) % cell survival at 37° C.: 10 µM Cisp/Quercetin/selenite 78.6%, 10 µM Cisp 37.5%.
- v) % cell survival at 42° C.: 10 µM Cisp/Quercetin/selenite 61%, 10 µM Cisp 37.5%.
- vi) Vitamin E did not seem to have additional effect on Cisp/Quercetin/Selenite treatment.

FIG. 4d shows that the combination of Quercetin and Selenite did not result in synergistic gains in effectiveness for the chemotherapeutic agent cisplatin. FIG. 4d also shows that the combination of Vit-E, Selenite, and Quercetin did not result in synergistic gains in effectiveness for the chemotherapeutic agent cisplatin.

Study 5:

Tested combinations of chemotherapeutic agents (Mitomycin C and Cisplatin at two different concentrations) and three non-chemotherapeutic agents (Vitamin D, Vitamin E, Selenite and Quercetin) with the human colon cancer cell line HCT-116 using MTS assays.

Figure 5A:
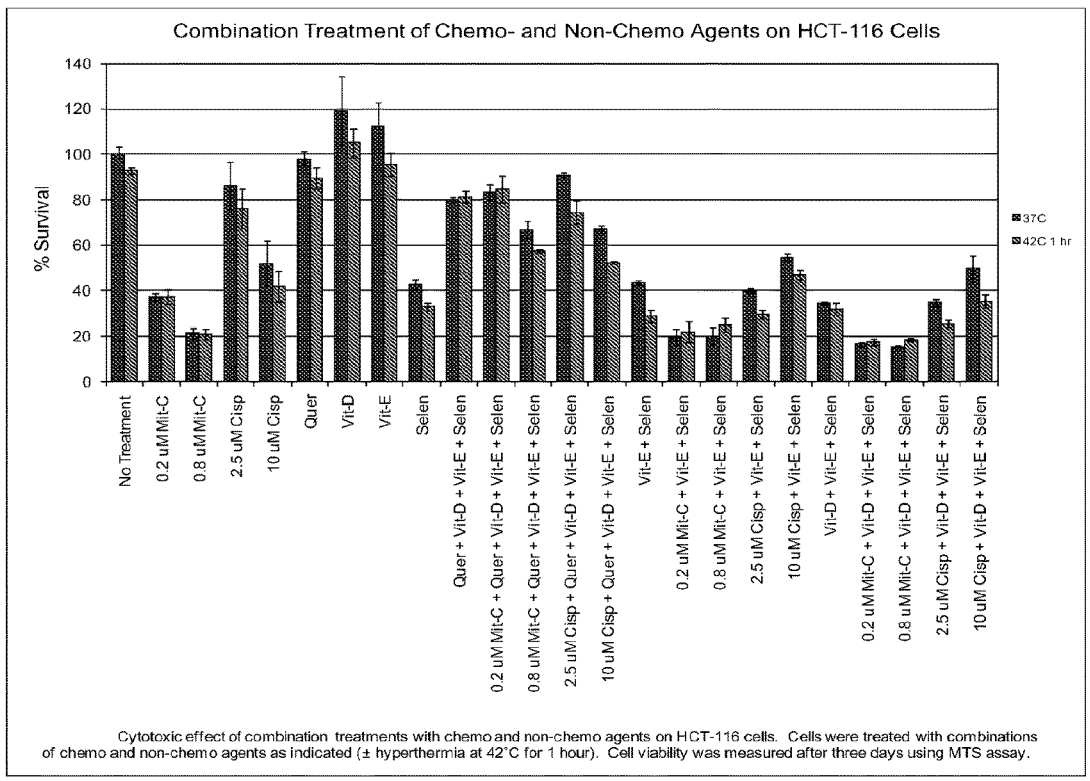

FIG. 5a: Hyperthermia Treatment had an Effect on:
- i) Control cells without treatment (solvent only control) (% cell survival of 37° C. vs 42° C. 1 hr treatment: 100% vs 92.7% at a significance level of P=0.05, one-tailed paired T-test).
- ii) 2.5 µM Cisplatin (% cell survival of 37° C. vs 42° C. 1 hr treatment: 86.1% vs 76.0% at a significance level of P=0.01, one-tailed paired T-test). 10 µM Cisplatin (% cell survival of 37° C. vs 42° C. 1 hr treatment: 52.1% vs 41.9% at a significance level of P=0.01, one-tailed paired T-test)
- iii) 150 µM Quercetin treatment (% cell survival of 37° C. vs 42° C. 1 hr treatment: 98.0% vs 89.5% at a significance level of P=0.02, one-tailed paired T-test).
- iv) 20 µM Selenite treatment (% cell survival of 37° C. vs 42° C. 1 hr treatment: 42.6% vs 32.9% at a significance level of P=0.02, one-tailed paired T-test).
- v) 40 µM Vitamin E treatment (% cell survival of 37° C. vs 42° C. 1 hr treatment: 112.2% vs 95.5% at a significance level of P=0.02, one-tailed paired T-test).
- vi) 0.8 µM Mitomycin C/Quercetin/Vit-D/Vit-E/Selenite treatment (% cell survival of 37° C. vs 42° C. 1 hr treatment: 66.9% vs 57.3% at a significance level of P=0.02, two-tailed paired T-test).
- vii) 2.5 µM Cisplatin/Quercetin/Vit-D/Vit-E/Selenite treatment (% cell survival of 37° C. vs 42° C. 1 hr treatment: 90.8% vs 74.4% at a significance level of P=0.02, one-tailed paired T-test). 10 Cisplatin/Quercetin/Vit-D/Vit-E/Selenite treatment (% cell survival of 37° C. vs 42° C. 1 hr treatment: 67.0% vs 52.3% at a significance level of P=0.002, one-tailed paired T-test).
- viii) Vit-E/Selenite treatment (% cell survival of 37° C. vs 42° C. 1 hr treatment: 43.5% vs 28.8% at a significance level of P=0.01, one-tailed paired T-test).
- ix) 2.5 µM Cisplatin/Vit-E/Selenite (% cell survival of 37° C. vs 42° C. 1 hr treatment: 39.9% vs 29.6% at a significance level of P=0.03, one-tailed paired T-test). 10 µM Cisplatin/Vit-E/Selenite treatment (% cell survival of 37° C. vs 42° C. 1 hr treatment: 54.7% vs 47.1% at a significance level of P=0.02, one-tailed paired T-test).
- x) 0.2 µM Mitomycin C/Vit-D/Vit-E/Selenite treatment (% cell survival of 37° C. vs 42° C. 1 hr treatment: 16.6% vs 17.5% at a significance level of P=0.02, two-tailed paired T-test). 0.8 µM Mitomycin C/Vit-D/Vit-E/Selenite treatment (% cell survival of 37° C. vs 42° C. 1 hr treatment: 15.2% vs 18.4% at a significance level of P=0.02, two-tailed paired T-test).
- xi) 2.5 µM Cisplatin/Vit-D/Vit-E/Selenite treatment (% cell survival of 37° C. vs 42° C. 1 hr treatment: 34.7% vs 25.7% at a significance level of P=0.01, one-tailed paired T-test).

FIG. 5a shows that the combination of Quercetin, Vit-D, Vit-E, and Selenite did not result in synergistic gains in effectiveness for the chemotherapeutic agents cisplatin or mitomycin. FIG. 5a does, however, demonstrate synergistic gains in the effectiveness of both cisplatin and mitomycin when they were administered in conjunction with the combination of Vit-D, Vit-E, and Selenite or in conjunction with the combination of Vit-E and Selenite.

Figure 5B:
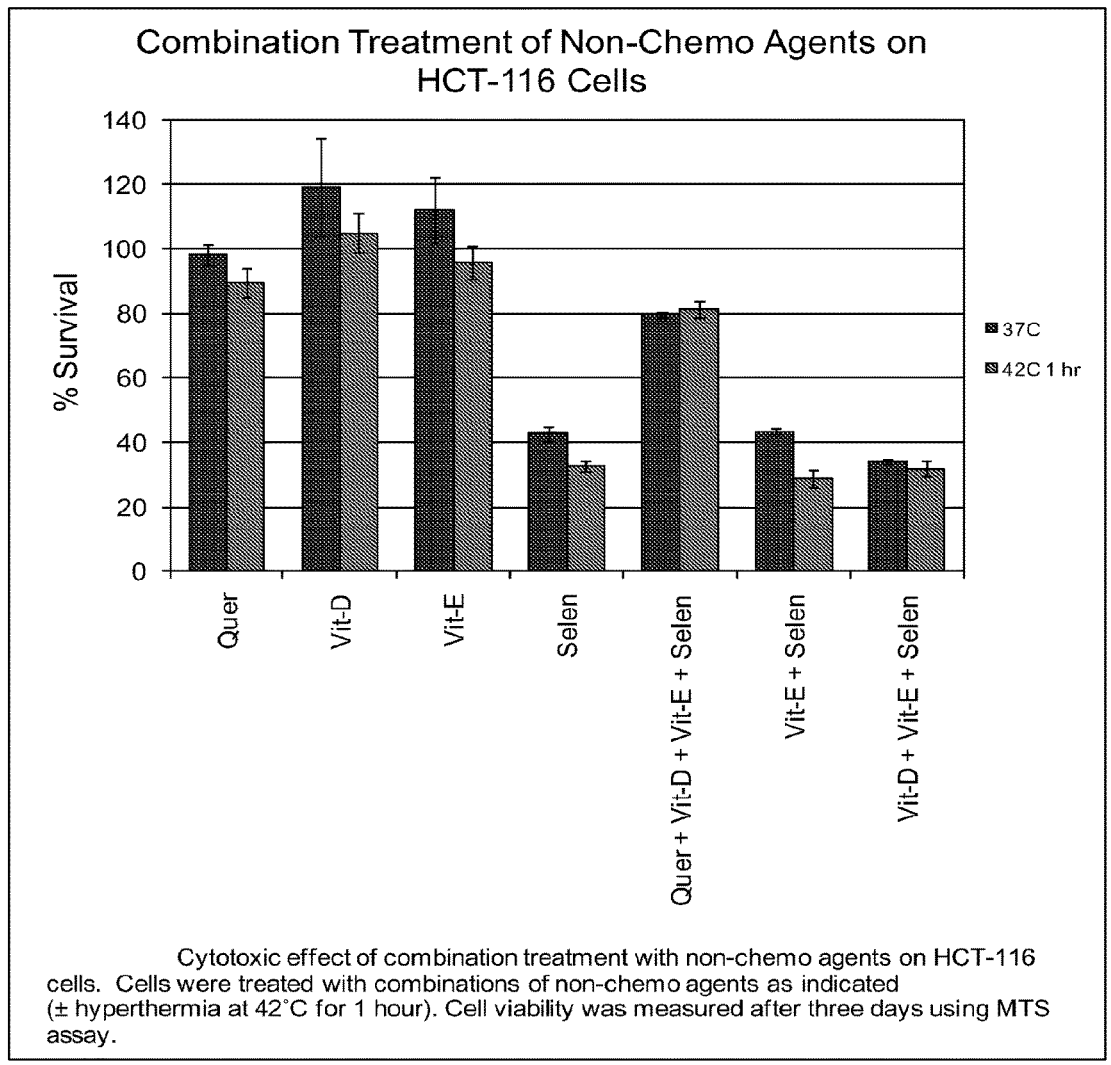

FIG. 5b:
- i) Quercetin reduced the cytotoxicity of Selenite/Vit-D/Vit-E. Neither Vitamin E alone nor the combination of Vitamin D/Vitamin E had little effect on reducing the cytotoxicity of Selenite.
- ii) % cell survival at 37° C.: Selenite 42.6%; Quercetin/Vit-D/Vit-E/Selenite 79.6%; Vit-E/Selenite 43.5%; Vit-D/Vit-E/Selenite 34.3%. % cell survival at 42° C.: Selenite 32.9%; Quercetin/Vit-D/Vit-E/Selenite 81.3%; Vit-E/Selenite 28.8%; Vit-D/Vit-E/Selenite 31.9%.

Figure 5C:
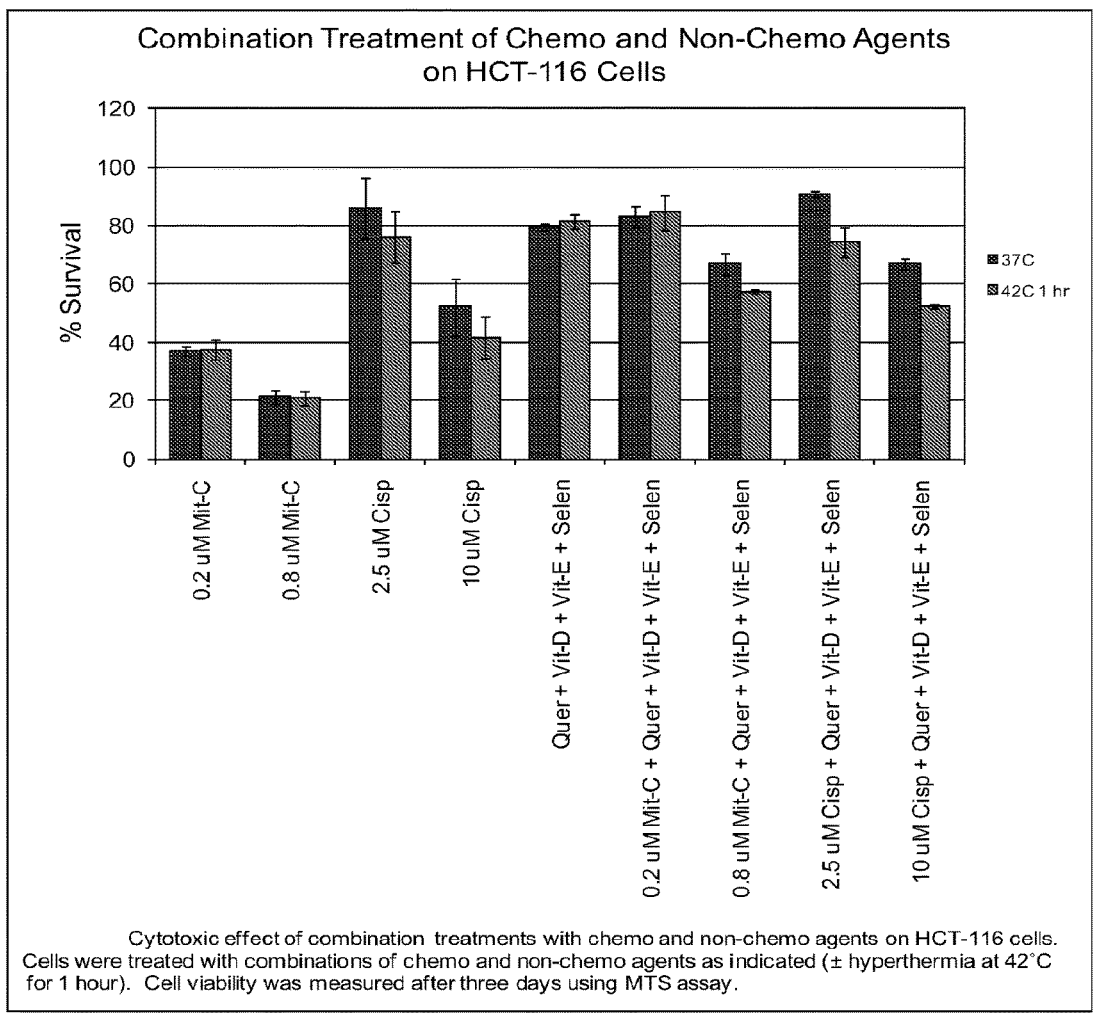

FIG. 5c: The addition of Quercetin/Vit-D/Vit-E/Selenite reduced the cytotoxicity of Mitomycin C on HCT-116 cells. This combination also reduced the cytotoxicity of Cisplatin. However, the effect was not as significant as that seen with Mitomycin C.

FIG. 5c shows that the combination of Quercetin/Vit-D/Vit-E/Selenite did not result in synergistic gains in effectiveness for the chemotherapeutic agents cisplatin or mitomycin.

Figure 5D:
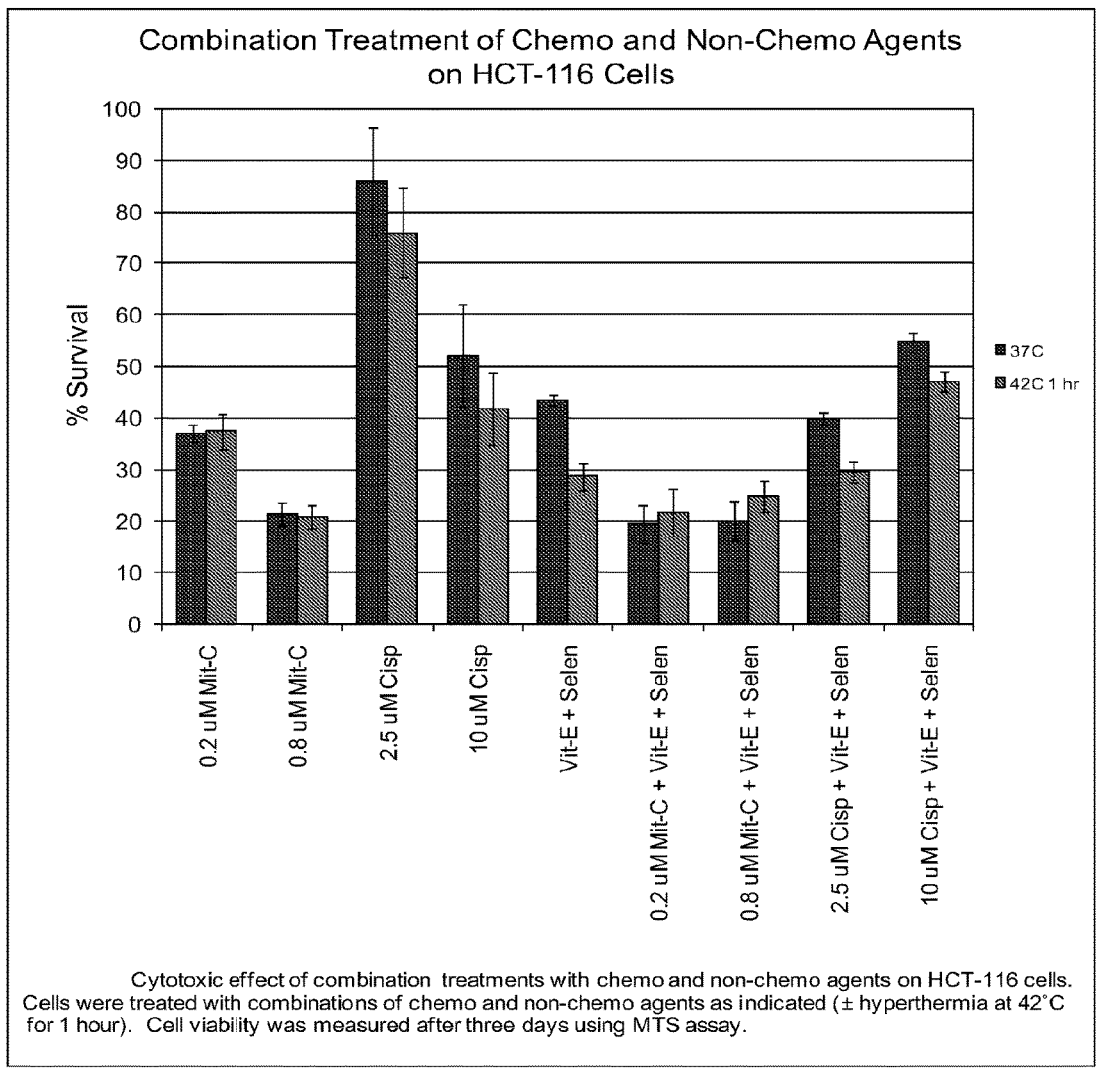

FIG. 5d: In contrast to the Quercetin/Vit-D/Vit-E/Selenite treatment (FIG. 5c), addition of Vit-E/Selenite did not significantly reduce the cytotoxicity caused by chemotherapeutic agents.

FIG. 5d shows that the combination of Vit-E/Selenite resulted in synergistic gains in effectiveness for mitomycin (at the 0.2 µM concentration) and for cisplatin at the 2.5 µM concentration.

FIG. 5e: In contrast to the Quercetin/Vit-D/Vit-E/Selenite treatment (FIG. 5c), addition of Vit-D/Vit-E/Selenite did not reduce the cytotoxicity caused by chemotherapeutic agents, suggesting that the Quercetin was a key component for such protective effects.

FIG. 5e shows that the combination of Vit-D/Vit-E/Selenite resulted in synergistic gains in effectiveness across chemotherapeutic concentrations, especially for mitomycin at the 0.2 µM concentration and for cisplatin at the 2.5 µM concentration.

Figure 6A:
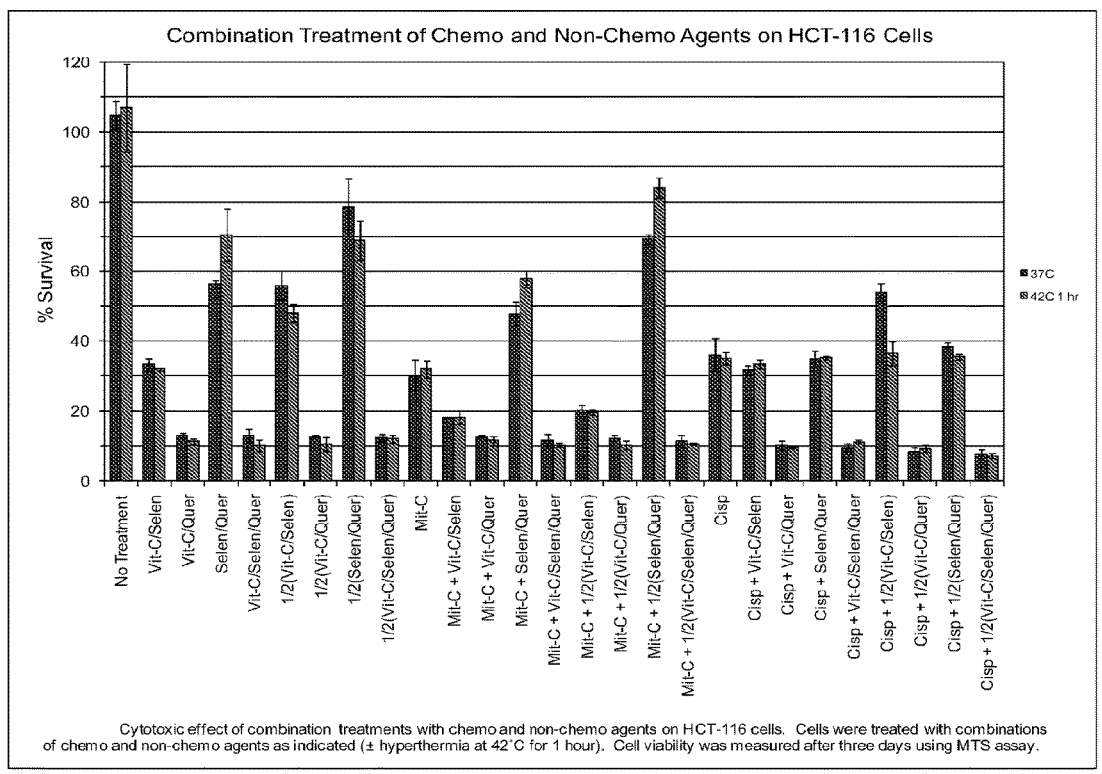
Figure 6B:
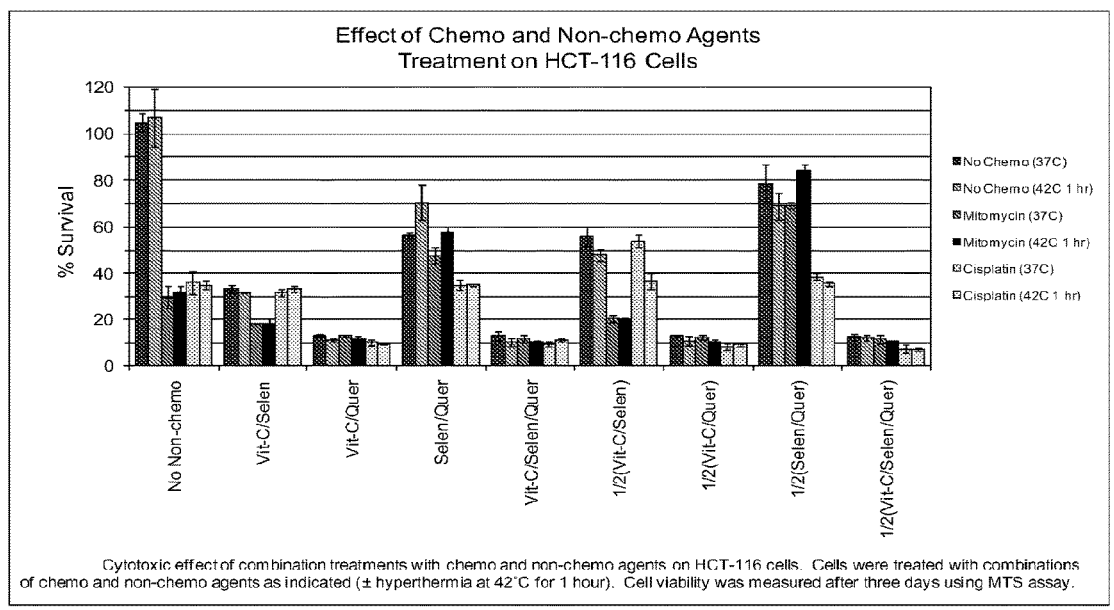

Study 6:

Tested the cytotoxic effects of combination treatments (±hyperthermia at 42° C. for one hour) with chemotherapeutic reagents (0.2 µM Mitomycin C or 10 µM Cisplatin) and three non-chemotherapeutic reagents (1.25 mM Vitamin C, 20 µM Selenite, and 150 µM Quercetin and also combinations with half of above concentrations). We found that the double combination of Vitamin C/Quercetin worked as well as the triple combination of Vitamin C/Selenite/Quercetin (either at the concentrations normally used or at the half of such) in killing HCT-116 cells, even without the presence of chemotherapeutic agents (FIGS. 6a and 6b). We did not observe the same killing effect with either Vit-C/selenite (FIG. 3) or selenite/Quercetin (FIG. 4) treatment, indicating such killing effects are specific for the Vit-C/Quercetin combination.

FIGS. 6a and 6b: Hyperthermia treatment had an effect on:
 i) 1.25 mM Vitamin C/150 µM Quercetin treatment (% cell survival of 37° C. vs 42° C. 1 hr treatment: 13.0% vs 11.2% at a significance level of P=0.05, one-tailed paired T-test).
 ii) 1.25 mM Vitamin C/20 µM Selenite/150 µM Quercetin treatment (% cell survival of 37° C. vs 42° C. 1 hr treatment: 12.9% vs 10.2% at a significance level of P=0.04, one-tailed paired T-test).
 iii) 0.625 mM Vitamin C/10 µM Selenite treatment (% cell survival of 37° C. vs 42° C. 1 hr treatment: 55.9% vs 48.0% at a significance level of P=0.04, one-tailed paired T-test).
 iv) 0.2 µM Mitomycin C/20 µM Selenite/150 µM Quercetin treatment (% cell survival of 37° C. vs 42° C. 1 hr treatment: 47.7% vs 57.8% at a significance level of P=0.01, two-tailed paired T-test).
 v) 0.2 µM Mitomycin C/10 µM Selenite/75 µM Quercetin treatment (% cell survival of 37° C. vs 42° C. 1 hr treatment: 69.3% vs 84.0% at a significance level of P=0.01, two-tailed paired T-test).
 vi) 10 µM Cisplatin/1.25 mM Vitamin C/20 µM Selenite/ 150 µM Quercetin treatment (% cell survival of 37° C. vs 42° C. 1 hr treatment: 9.5% vs 11.2% at a significance level of P=0.05, two-tailed paired T-test).
 vii) 10 µM Cisplatin/0.625 mM Vitamin C/10 µM Selenite treatment (% cell survival of 37° C. vs 42° C. 1 hr treatment: 54.0% vs 36.5% at a significance level of P=0.01, one-tailed paired T-test).
 viii) 10 µM Cisplatin/10 µM Selenite/75 µM Quercetin treatment (% cell survival of 37° C. vs 42° C. 1 hr treatment: 38.5% vs 35.6% at a significance level of P=0.02, one-tailed paired T-test).

FIG. 6a shows that the combinations of Vit-C/Selenite, Vit-C/Quercetin, and Vit-C/Quercetin/Selenite resulted in synergistic gains in cancer cell killing effectiveness, whereas the combination of Selinite/Quercetin did not appear to exert significant synergistic killing effects. The same combinations of Vit-C/Selenite, Vit-C/Quercetin, and Vit-C/Quercetin/Selenite resulted in synergistic gains when applied in conjunction with both mitomycin and cisplatin across varied concentrations.

Figure 6C:
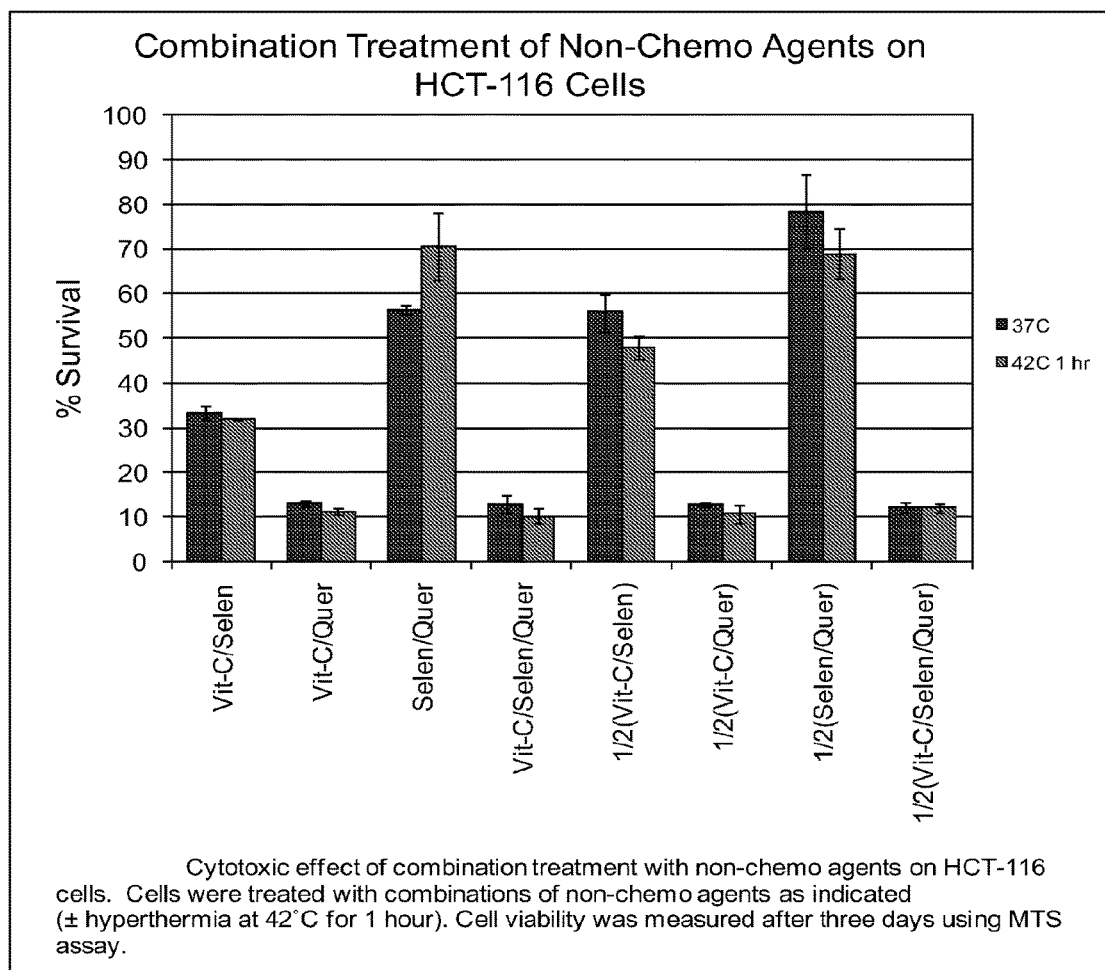

FIG. 6c:
 i) Vit-C/Quercetin, even at only half of the other test concentrations (0.625 mM Vitamin C and 75 µM Quecertin), exerted a similar killing effect as the triple combination of Vit-C/Selenite/Quercetin.
 ii) % cell survival: 1.25 mM Vitamin C/150 µM Quercetin 13.0% at 37° C. and 11.2% at 42° C.; 1.25 mM Vitamin C/20 µM Selenite/150 µM Quercetin 12.9% at 37° C. and 10.2% at 42° C.; 0.625 mM Vitamin C/75 µM Quercetin 12.8% at 37° C. and 10.6% at 42° C. 0.625 mM Vitamin C/10 µM Selenite/75 µM Quercetin 12.3% at 37° C. and 12.0% at 42° C.
 iii) Similar to previous results, Vitamin C did not appear to modulate the cytotoxicity caused by Selenite (see FIG. 3b), while Quercetin reduced the cytotoxicity caused by Selenite (see FIG. 4b).

FIGS. 6b and 6c demonstrate that the combinations of Vit-C/Quercetin and Vit-C/Quercetin/Selenite result in synergistic gains in cancer cell killing effectiveness, both alone or in conjunction with either mitomycin or cisplatin. Vit-C/ Selenite or Selenite/Quercetin combinations did not show the same magnitudes of synergy.

Study 7:
Tested the short term cytotoxic effect of double and triple combination treatments on HCT-116 cells.

Figure 7A:
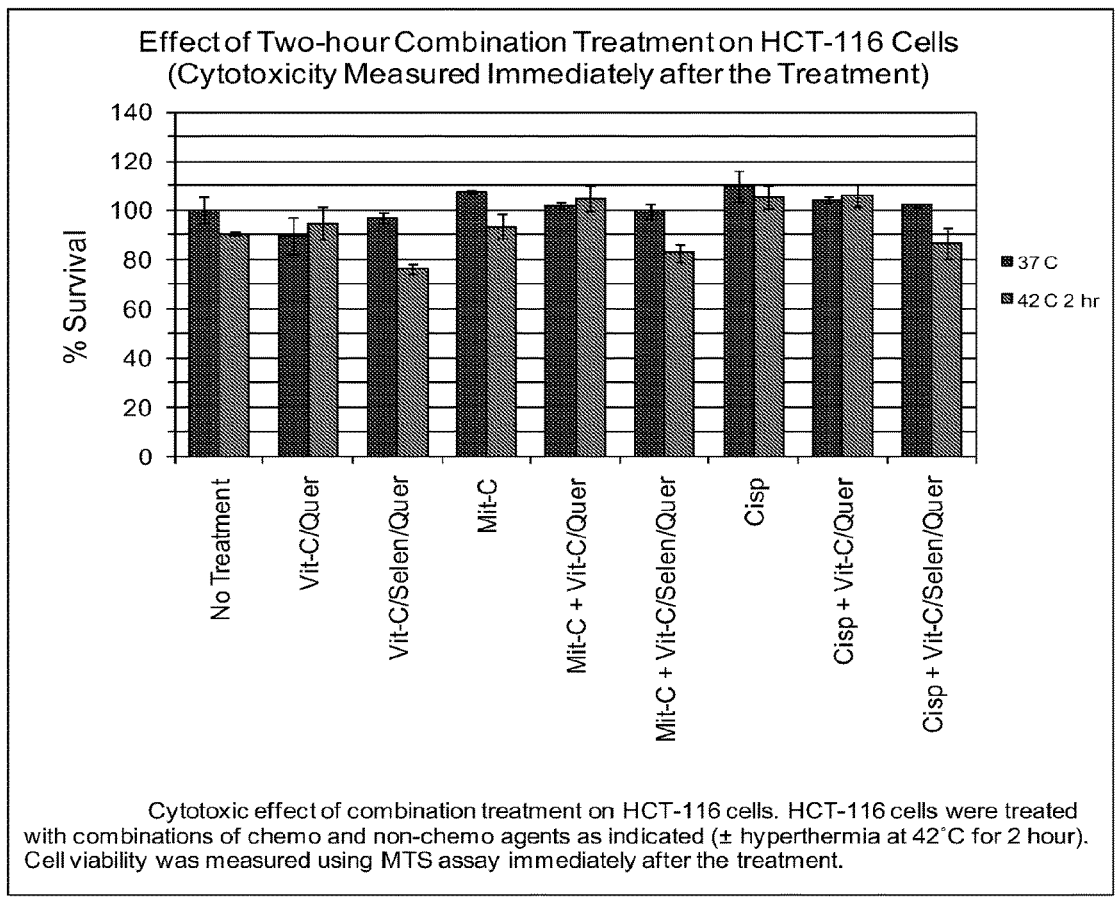

FIG. 7a:
 i) Only the combination of Vit-C/Selenite/Quercetin treatment in conjunction with hyperthermia (either with or without chemotherapeutic agents) had a consistent and significant cytotoxic effect on HCT-116 cells immediately after just two hours of testing treatments.
 ii) Vit-C/Selenite/Quercetin treatment (% cell survival of 37° C. vs 42° C. 2 hr treatment: 97.1% vs 76.1% at a significance level of P=0.001, one-tailed paired T-test); Mit-C/Vit-C/Selenite/Quercetin treatment (% cell survival of 37° C. vs 42° C. 2 hr treatment: 99.6% vs 82.8% at a significance level of P=0.01, one-tailed paired T-test); Cisplatin/Vit-C/Selenite/Quercetin treatment (% cell survival of 37° C. vs 42° C. 2 hr treatment: 102% vs 86.7% at a significance level of P=0.02, one-tailed paired T-test).

FIG. 7a demonstrates that after just a 2 hours treatment window, the only combination that showed rapid synergistic gains in cancer cell killing effectiveness, alone or in conjunction with either mitomycin or cisplatin, was Vit-C/ Quercetin/Selenite.

Figure 7B:
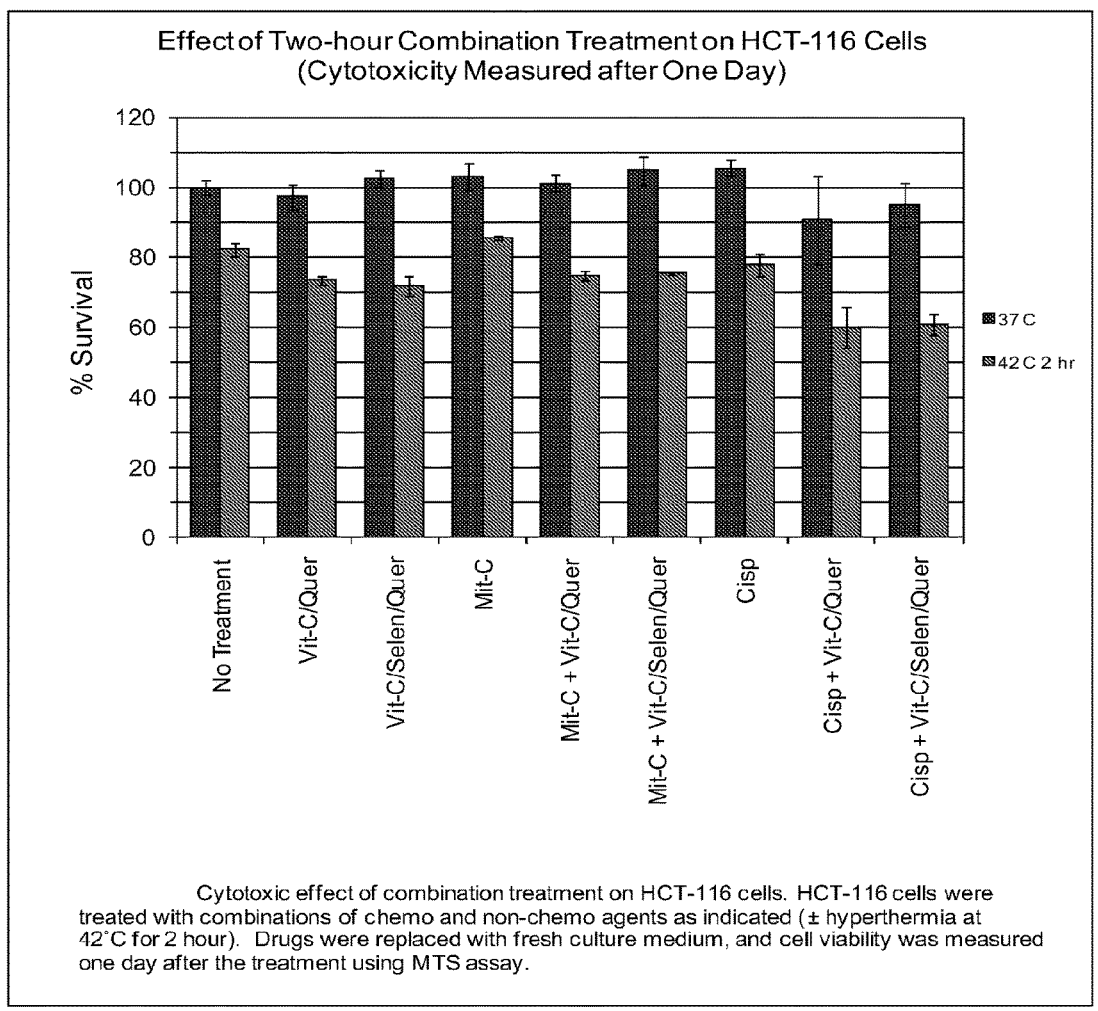

FIG. 7b:
 i) Hyperthermia treatment (extended from one hour to two hours) had a significant cytotoxic effect (20 to 40% cell killing depending on the treatments) on HOT-116 cells.
 ii) Without hyperthermia, combination treatments for two hours was not sufficient to exert cytotoxic effects (compare all treatment groups at 37° C. to no treatment at 37° C.).
 iii) Two-hour combination treatment with non-chemotherapeutic agents at 42° C. for 2 hr had an additive effect to hyperthermia treatment alone. % cell survival of 42° C. 2 hr treatment groups: No treatment vs Vit-C/Quercetin: 82.2% vs 73.6% at a significance level of P=0.02, one-tailed paired T-test; No treatment vs Vit-C/Selenite/Quercetin: 82.2% vs 71.8% at a significance level of P=0.03, one-tailed paired T-test).
 iv) Only Cisplatin had an additional killing effect on non-chemotherapeutic combination treatments. % cell survival of 42° C. 2 hr treatment groups: Vit-C/Quercetin vs Cisplatin/Vit-C/Quercetin: 73.4% vs 60.1% at a significance level of P=0.02, one-tailed paired T-test; Vit-C/Selenite/Quercetin vs Cisplatin/Vit-C/Selenite/ Quercetin: 71.8% vs 60.9% at a significance level of P=0.03, one-tailed paired T-test. Vit-C/Quercetin vs Mitomycin C/Vit-C/Quercetin: 73.4% vs 74.7%, not significant via a one-tailed paired T-test; Vit-C/Selenite/ Quercetin vs Mitomycin C/Vit-C/Selenite/Quercetin: 71.8% vs 75.4% not significant via one-tailed paired T-test.
 v) Without hyperthermia, incubating cells with drugs for two hours was not sufficient to cause cytotoxicity (compare to the result in FIG. 7c, where one-day drug treatment without hyperthermia caused 60 to 65% cytotoxicity).

FIG. 7b demonstrates that after just 2 hours of treatment, the combinations of Vit-C/Quercetin and Vit-C/Selenite/ Quercetin showed synergistic gains (cell survivals measured one day later) in cancer cell killing effectiveness, alone or in conjunction with either mitomycin or cisplatin.

Figure 7C:
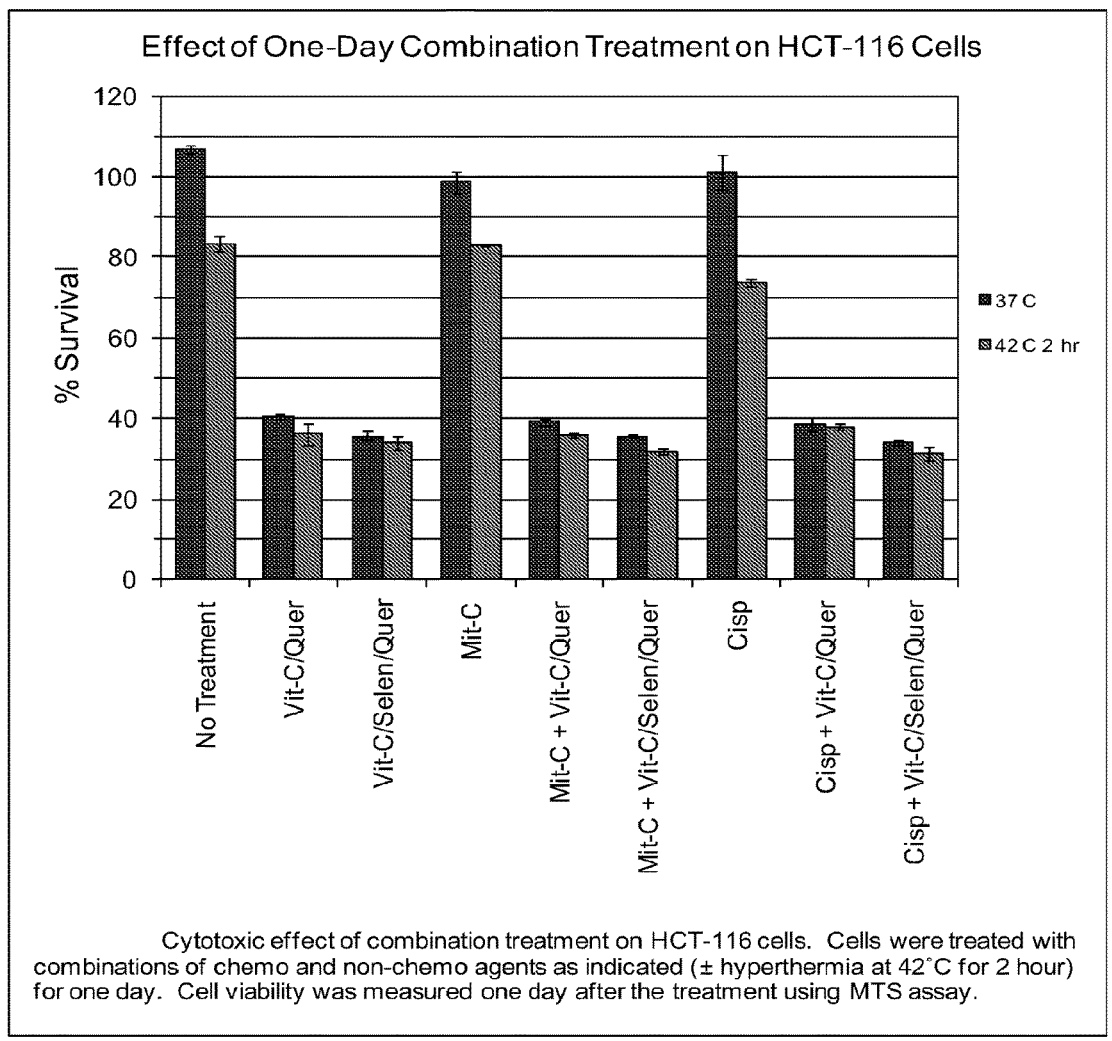

FIG. 7c:
i) One-day combo treatments (either with or without hyperthermia) caused significant cytotoxicity (~60 to 70%) either with or without hyperthermia treatment (note: 3-day combo treatments led to ~90% cell death in previous experiments).
ii) The triple combination of non-chemotherapeutic agents (Vit-C/Selenite/Quercetin) had a slight, but significant, increase over the double combination treatment (Vit-C/Quercetin). Such effects were seen after the one-day drug incubation assay, but not in the two-hour treatment assay (FIG. 7b).

FIG. 7c demonstrates that after 24 hours of treatment, the combinations of Vit-C/Quercetin and Vit-C/Selenite/Quercetin showed synergistic gains in cancer cell killing effectiveness, alone or in conjunction with either mitomycin or cisplatin.

Study 8:
Tested the cytotoxic effect of short-term combination treatment on HCT-116 cells.
i) The cytotoxic effect of two-hour combination treatment (±hyperthermia) on HCT-116 cells was more prominent after three days (FIG. 8) than that after one day (FIG. 7b)
ii) Even without hyperthermia, two-hour combination treatments were sufficient to exert cytotoxic effects on HCT-116 cells after three days (compare all treatment groups without hyperthermia to the control no treatment group in FIG. 8).
iii) Hyperthermia treatment at 42° C. for two hours significantly increased the cytotoxic effects of combination treatments after three days (compare all treatment group with and without hyperthermia in FIG. 8).
iv) Chemotherapeutic agents further increased the cytotoxic effect of double and triple treatments (FIG. 8). % cell survival without hyperthermia treatment: Vit-C/Quercetin 64%, Mit-C/Vit-C/Quercetin 44.3%, Cisplatin/Vit-C/Quercetin 26.9%, Vit-C/Selenite/Quercetin 63.3%, Mit-C/Vit-C/Selenite/Quercetin 48.2%, Cisplatin/Vit-C/Selenite/Quercetin 29.8%; % cell survival with hyperthermia treatment: Vit-C/Quercetin 28.4%, Mit-C/Vit-C/Quercetin 21.8%, Cisplatin/Vit-C/Quercetin 12.6%, Vit-C/Selenite/Quercetin 29.4%, Mit-C/Vit-C/Selenite/Quercetin 22.3%, Cisplatin/Vit-C/Selenite/Quercetin 14%.

Figure 8:
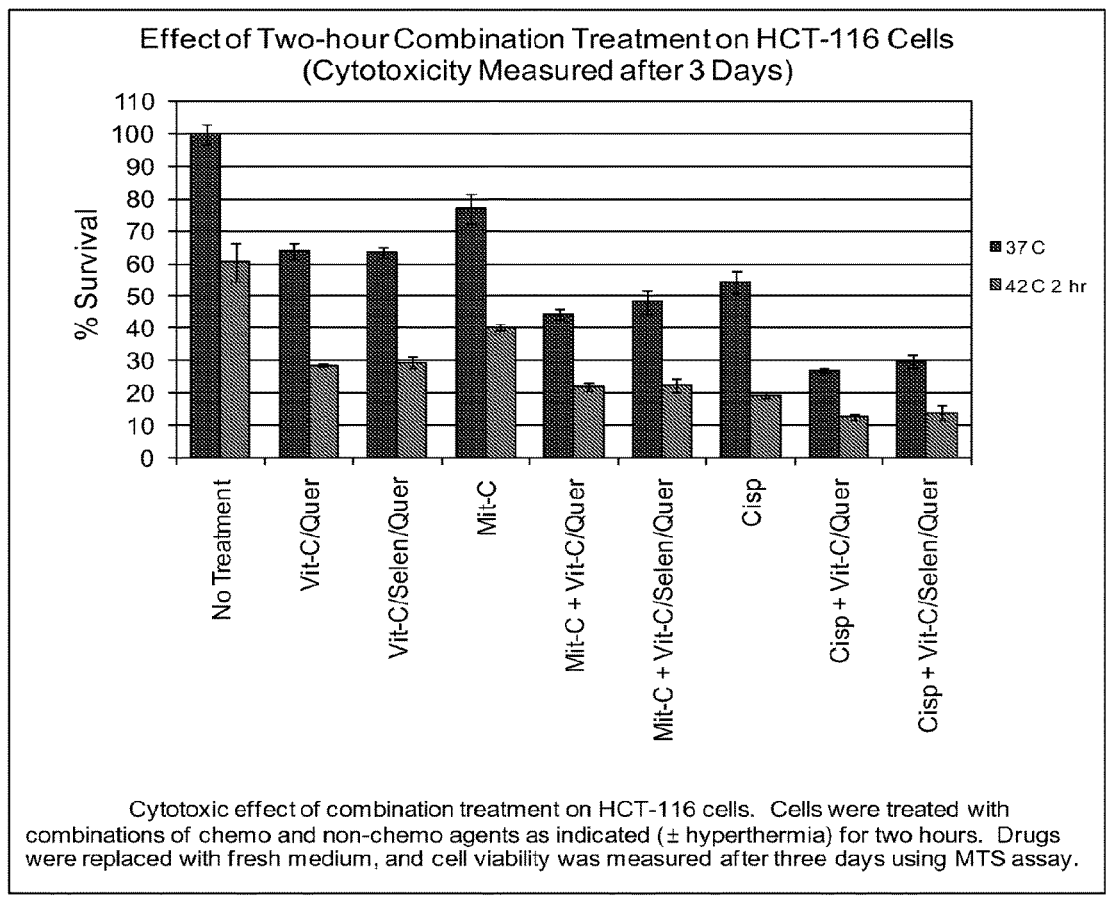

FIG. 8 demonstrates that after just 2 hours of treatment, the combinations of Vit-C/Quercetin and Vit-C/Selenite/Quercetin showed synergistic gains (cell survivals measured three days later) in cancer cell killing effectiveness, alone or in conjunction with either mitomycin or cisplatin.

Said chemicals, and/or mimetics or derivatives thereof, either as single chemicals or in a mixture, obtained via methods outlined herein or other methods that are appreciated by those skilled in the art, are administered to an individual, said individual having been identified as afflicted with cancer, in a pharmaceutically effective amount.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A pharmaceutical composition comprising a synergistic combination of compounds present in synergistically effective amounts, wherein the synergistic combination is a combination consisting of (i) from 0.625 mM to 1.25 mM Vitamin C and from 75 µM to 150 µM quercetin or (ii) 0.625 mM to 1.25 mM Vitamin C, from 10 µM to 20 µM selenium and from 75 µM to 150 µM quercetin; wherein both of said combinations yield a synergistic effect on killing colorectal carcinoma cells.

2. The pharmaceutical composition according to claim 1, further comprising a chemotherapeutic agent.

3. The pharmaceutical composition according to claim 2, wherein the chemotherapeutic agent is selected from the group consisting of cisplatin, carboplatin, mitomycin, vincristine, methotrexate, fluorouracil, calcium foliate, cytosine arabinoside, cyclophosphamide, epirubicin, bleomycin A5, taxanes, mitoxanthrone, topoisomerase inhibitors, angiogenesis inhibitors, busulfan, doxorubicin, and tamoxifen.

4. The pharmaceutical composition according to claim 1, wherein the synergistic combination is Vitamin C and quercetin.

5. The pharmaceutical composition according to claim 1, wherein the synergistic combination is Vitamin C, selenium and quercetin.

6. A pharmaceutical composition comprising a synergistic combination of compounds present in synergistically effective amounts, wherein the synergistic combination is (i) a combination of compounds consisting of from 0.625 mM to 1.25 mM Vitamin C and from 75 µM to 150 µM quercetin and a chemotherapeutic agent, or (ii) a combination of compounds consisting of from 0.625 mM to 1.25 mM Vitamin C, from 10 µM to 20 µM selenium, from 75 µM to 150 µM quercetin and a chemotherapeutic agent wherein said synergistic combination is effective at killing colorectal carcinoma cells.

7. The pharmaceutical composition according to claim 6, wherein the chemotherapeutic agent is selected from the group consisting of cisplatin, carboplatin, mitomycin, vincristine, methotrexate, fluorouracil, calcium folinate, cytosine arabinoside, cyclophosphamide, epirubicin, bleomycin A5, taxanes, mitoxanthrone, topoisomerase inhibitors, angiogenesis inhibitors, busulfan, doxorubicin, and tamoxifen.

8. The pharmaceutical composition according to claim 7, wherein the chemotherapeutic agent is cisplatin.

9. The pharmaceutical composition according to claim 8, wherein the synergistic combination is a combination of compounds consisting of from 0.625 mM to 1.25 mM Vitamin C, from 10 µM to 20 µM selenium, from 75 µM to 150 µM quercetin and from 2.5 µM to 10 µM cisplatin.

10. The pharmaceutical composition according to claim 7, wherein the chemotherapeutic agent is mitomycin.

11. The pharmaceutical composition according to claim 10, wherein the synergistic combination is a combination of compounds consisting of from 0.625 mM to 1.25 mM Vitamin C, from 10 µM to 20 µM selenium, from 75 µM to 150 µM quercetin and from 0.2 µM to 0.8 µM mitomycin.

12. The pharmaceutical composition according to claim 6, wherein said pharmaceutical composition further comprises a sterile solution.

13. The pharmaceutical composition according to claim 12, wherein the sterile solution is a sterile saline solution.

* * * * *